US012758491B2

(12) United States Patent
Janagam et al.

(10) Patent No.: US 12,758,491 B2
(45) Date of Patent: Oct. 13, 2026

(54) POLYMERIC LEUPROLIDE ACETATE FORMULATIONS

(71) Applicant: Tolmar International Limited, Dublin (IE)

(72) Inventors: Dileep Janagam, San Ramon, CA (US); David Dummer, Firestone, CO (US); Travis Kauffman, Fort Collins, CO (US); John Middleton, Fort Collins, CO (US); Amy Van Hove, Fort Collins, CO (US); Nicole Marquardt, Fort Collins, CO (US); Nicholas DeWeerd, Fort Collins, CO (US); Erik Cullen Johnson, Fort Collins, CO (US)

(73) Assignee: Tolmar International Limited, Dublin (IE)

( * ) Notice: Subject to any disclaimer, the term of this patent is extended or adjusted under 35 U.S.C. 154(b) by 0 days.

(21) Appl. No.: 19/362,588

(22) Filed: Oct. 20, 2025

(65) Prior Publication Data

US 2026/0069531 A1 Mar. 12, 2026

Related U.S. Application Data

(63) Continuation of application No. PCT/IB2024/056487, filed on Jul. 3, 2024.

(60) Provisional application No. 63/512,016, filed on Jul. 5, 2023.

(51) Int. Cl.

| | |
|---|---|
| ***A61K 9/00*** | (2006.01) |
| ***A61K 9/06*** | (2006.01) |
| ***A61K 38/09*** | (2006.01) |
| ***A61K 47/22*** | (2006.01) |
| ***A61K 47/34*** | (2017.01) |

(52) U.S. Cl.
CPC .............. *A61K 9/0024* (2013.01); *A61K 9/06* (2013.01); *A61K 38/09* (2013.01); *A61K 47/22* (2013.01); *A61K 47/34* (2013.01)

(58) Field of Classification Search
CPC ........ A61K 9/0024; A61K 9/06; A61K 38/09; A61K 47/22; A61K 47/34
See application file for complete search history.

(56) References Cited

U.S. PATENT DOCUMENTS

| | | | |
|---|---|---|---|
| 4,938,763 | A | 7/1990 | Dunn et al. |
| 5,324,519 | A | 6/1994 | Dunn et al. |
| 5,702,716 | A | 12/1997 | Dunn et al. |
| 5,744,153 | A | 4/1998 | Yewey et al. |
| 5,990,194 | A | 11/1999 | Dunn et al. |
| 6,565,874 | B1 | 5/2003 | Dunn et al. |
| 6,773,714 | B2 | 8/2004 | Dunn et al. |
| 8,470,359 | B2 | 6/2013 | Dunn |
| 8,486,455 | B2 | 7/2013 | Dunn et al. |
| 8,840,916 | B2 | 9/2014 | Dunn |
| 9,254,307 | B2 | 2/2016 | Dunn et al. |
| 9,283,282 | B2 | 3/2016 | Dunn |
| 9,539,333 | B2 | 1/2017 | Dunn |
| 9,914,802 | B2 | 3/2018 | Dunn |
| 10,047,193 | B2 | 8/2018 | Dunn |
| 2006/0019903 | A1 | 1/2006 | Kuzma |
| 2008/0194663 | A1 | 8/2008 | Dunn |
| 2013/0288968 | A1 | 10/2013 | George et al. |
| 2014/0035757 | A1 | 2/2014 | Ramones et al. |
| 2015/0150937 | A1 | 6/2015 | Dunn et al. |
| 2015/0196485 | A1 | 7/2015 | Rodriguez et al. |
| 2015/0297726 | A1 | 10/2015 | Yoon et al. |
| 2016/0033180 | A1 | 2/2016 | Russo et al. |
| 2016/0106805 | A1 | 4/2016 | Dunn et al. |
| 2016/0106847 | A1 | 4/2016 | Dadey et al. |
| 2017/0096524 | A1 | 4/2017 | Dunn |
| 2020/0330547 | A1 | 10/2020 | Nangia et al. |
| 2020/0390849 | A1 | 12/2020 | Li et al. |
| 2022/0026576 | A1 | 1/2022 | Baribault et al. |
| 2022/0331523 | A1 | 10/2022 | Sherman et al. |
| 2023/0057569 | A1 | 2/2023 | Jadhav et al. |

FOREIGN PATENT DOCUMENTS

| | | |
|---|---|---|
| DE | 202009010095 | 10/2009 |
| EP | 3975990 | 4/2022 |
| KR | 102162217 | 10/2020 |
| WO | 2020240417 | 3/2020 |
| WO | 2023126463 | 7/2023 |

OTHER PUBLICATIONS

Partsch et al. "Management and outcome of central precocious puberty", Clinical Endocrinology, vol. 56 (2002), pp. 129-148.
Prasad et al. "Evaluation of GnRH analogues in diagnosis and management of children with pubertal disorders", Indian Journal of Endocrinology and Metabolism (May-Jun. 2012), vol. 16, No. 3, pp. 400-405.
"Supprelin La (histrelin acetate) FDA Label", FDA (May 2017) 20 pages.
"Triptodur (triptorelin) FDA Label", FDA (Jun. 2017), 13 pages.
Bellet et al. "Twelve-Month Estrogen Levels in Premenopausal Women With Hormone Receptor-Positive Breast Cancer Receiving Adjuvant Triptorelin Plus Exemestane or Tamoxifen in the Suppression of Ovarian Function Trail (SOFT): The SOFT-EST Substudy," Journal of Clinical Oncology, vol. 34, No. 14 (May 10, 2016), 25 pages.
Clowse, et al. "Ovarian Preservation by GnRH Agonists during Chemotherapy: A Meta_Analysis," Journal of Women's Health, vol. 18, No. 3 (2009), pp. 311-319.
Lambertini , et al. "Conadotropin-Releasing Hormone Agonists During Chemotherapy for Preservation of Ovarian Function and Fertility in Premenopausal Patients With Early Breast Cancer: A Systematic Review and Meta-Analysis of Individual Patient-Level Data," Journal of Clinical Onocology, vol. 36, No. 19 (Jul. 1, 2018), pp. 1981-1990 (12 pages).

(Continued)

*Primary Examiner* — Robert A Wax
*Assistant Examiner* — Olga V. Tcherkasskaya
(74) *Attorney, Agent, or Firm* — Ballard Spahr LLP

(57) ABSTRACT

Liquid-liquid polymer leuprolide acetate (LA) formulations comprising a biodegradable polymer and biocompatible solvent, and methods of using the formulations.

24 Claims, 13 Drawing Sheets

(56) References Cited

OTHER PUBLICATIONS

Lambertini et al. "Ovarian suppression using luteinizing hormone-releasing agonists during chemotherapy to preserve ovarian function and fertility of breast cancer patients: a meta-analysis of randomized studies," Annals of Oncology 26: 2408-2419 (2015) (Year:2015).
Lauretta, et al. "Gender in Endocrine Diseases: Role of Sex Gonadal Hormones," International Journal of Endocrinology, vol. 2018, Published Oct. 21, 2018 (11 pages).
Leuproelin acetate from the preservation of ovarian function in premenopausal women with neoplastic disease undergoing chemotherapy NIHR Innovation Observatory Evidence Briefing (Jul. 2018), NIHRO (HSRIC) ID: 24223 (9 pages).
Luan, X. et al. "Influence of the poly(lactide-co-glycolide) type on the leuprolide release from in situ forming microparticle systems", Journal of Controlled Release, Elsevier, Amsterdam, NL, vol. 110, No. 2 (Jan. 10, 2006), pp. 266-272.
Kurebayashi et al., "Efficacy and safety of leuprorelin acetate 6-month depot, TAP-144-SR (6M), in combination with tamoxifen in postoperative, premenopausal patients with hormone receptor-positive breast cancer: a phase III, randomized, open-label, parallel-group comparative study," Breast Cancer, vol. 24, Mar. 26, 2016, pp. 161-170.
Nelson, et al. "Estrogen production and action," American Academy of Dermatology, vol. 45, No. 3 (9 pages).
Ravivarapu et al. "Sustained Activity and Release of Leuprolide Acetate from an In Situ Forming Polymeric Implant," AAPS PharmSciTech, 2000, vol. 1, No. 1, article 1, 8 pages.
Ravivarapu et al. "Sustained Suppression of Pituitary-Gonadal Axis with an Injectable, In Situ Forming Implant of Leuprolide Acetate," Journal of Pharmaceutical Sciences, Jun. 2000, vol. 89, No. 6, pp. 732-741.
Sartor et al. "An Eight-Month Clinical Study of LA-2575 30.0 mg: A New 4-Month, Subcutaneous Delivery System for Leuprolide Acetate in the Treatment of Prostate Cancer," Adult Urology 62 (2), 2003, 5 pages.
Song et al. "Effect of leuprolide acetate on ovarian function after cyclophosphamide-doxorubicin-based chemotherapy in premenopausal patients with breast cancer: results from a phase II randomized trial," Med. Oncol (2013) 30:667, published Aug. 1, 2013 (8 pages).
Schmid et al., "Leuprorelin Acetate Every-3-Months Depot Versus Cyclophosphamide, Methotrexate, and Fluorouracil as Adjuvant Treatment in Premenopausal Patients With Node-Positive Breast Cancer: The TABLE Study," Journal of Clinical Oncology, vol. 25, No. 18, Jun. 20, 2007, pp. 2509-2515.
Tesch et al. "Estrongen levels in young women with hormone receptor-positive breast cancer on ovarian function supression therapy," NPJ Breast Cancer (2024) 10:67 (8 pages).
Antoniazzi, et al. "Central Precocious Puberty: Current Treatment Options", Pediatric Drugs, vol. 6, No. 4 (Jul. 2004), pp. 211-231.
Badaru et al. "Sequential Comparisons of One-Month and Three-Month Depot Leuprolide Regimens in Central Precocious Puberty", The Journal of Clinical Endocrinology & Metabolism, vol. 91, No. 5, pp. 1862-1867.
Carel et al. "Precocious Puberty", The New England Journal of Medicine, vol. 358, No. 22 (May 2008), pp. 2366-2377.
Carel. "precocious puberty and structural growth", Human Reproduction Update, vol. 10, No. 2 (2004), pp. 135-147.
Carel et al. "Treatment of Central Precocious Puberty by Subcutaneous Injections of lueproelin 3-Month Depot (11.25 mg)", The Journal of Clinical Endocrinology & Metabolism, vol. 87, No. 9 (2002), pp. 4111-4116.
Carretto, et al. "The Usefulness of the Leuprolide Stimulation Test as a Diagnostic Method of Idiopathic Central Precocious Puberty in Girls", Hormone and Metabolic Research, vol. 46, No. 13 (2014), pp. 959-963.
"E11(R1) Addendum: Clinical Investigation of Medicinal Products in the Pediatric Population Guidance for Industry", U.S. Department of Health and Human Services Food and Drug Administration, Apr. 2018, 14 pages.
Freire, et al. "High diagnostic accuracy of subcutaneous Triptorelin test compared with GnRH test for diagnosing cental precocious puberty in girls", Clinical Endocrinology, vol. 78 (2013), pp. 398-404.
Fuld, et al. "A Randomized Trial of 1- and 3-Month Depoty Leuprolide Doses in the Treatment of Central Precocious Puberty", The Journal of Pediatrics, vol. 159, No. 6 (Dec. 2011), pp. 982-987.
Fuqua. "Treatment and Outcomes of Precocious Puberty: An Update", The Journal of Clinical Endocrinology & Metabolism, vol. 98, No. 6 (Jun. 2013), pp. 2198-2207.
Ghai, et al. "Gonadotropin Releasing Hormone Agonist (Nafarelin) Test to Differentiate Gonadotropin Deficiency from Constitutionally Delayed Puberty in Teen-age Boys—A Clinical Research Study", Journal of Clinical Endocrinology and Metabolism, vol. 80, No. 10 (1995), pp. 2980-2986.
Guideline on pharmaceutical development of medicines for paediatric use, European Medicines Agency, Aug. 2013, EMA/CHMP/QWP/805880/2012 Rev. 2, 24 pages.
Houk, et al. "The Diagnostic Value of a Brief GnRH Analogue Stimulation Test in Girls with Central Precocious Puberty: A Single 30-minute Post-stimulation LH Sample is Adequate", Journal of Pediatric Endocrinology & Metabolism, vol. 21, No. 12 (2008), pp. 1113-1118.
Ibanez et al. "Use of leuprolide acetate response patterns in the early diagnosis of pubertal disorders: comparison with the gonadotropin-releasing hormone test", The Journal of Clinical Endocrinology and Metabolism, vol. 78, No. 1 (Jan. 1994), pp. 30-35. (abstract).
Kim, et al. "Multicenter clinical trial of leuprolide acetate depot (Luphere depot 3.75 mg) for efficacy and safety in girls with central precocious puberty", Annals of Pediatric Endocrinology & Metabolism, vol. 18, No. 4 (Dec. 2013), pp. 173-178.
Lee et al. "Morning basal leutinizing hormone, a good screening tool for diagnosing precocious puberty", Annals of Pediatric Endocrinology & Metabolism, vol. 24, No. 1 (Mar. 2019), pp. 27-33.
Lee, et al. "36-month Treatment Experience of Two Doses of Leuprolide Acetate 3-Month Depot for Children with Central Precocious Puberty", The Journal of Clinical Endocrinology & Metabolism, vol. 99, Issue 9 (Sep. 1, 2014), pp. 3153-3159.
"Lupron Depot-PED (leuprolide acetate for depot suspension)", FDA Label, FDA (Jun. 2014), 31 pages.
"Lupron Depot-PED (leuprolide acetate for depot suspension)", FDA Label, FDA (May 2017), 22 pages.
Mahmood. "Dosing in Children: A Critical Review of the Pharmacokinetic Allometric Scaling and Modelling Approaches in Paediatric Drug Development and Clinical Settings", Clinical Pharmacokinetics (2014), vol. 53, pp. 327-346.
Menon. "Precocious Puberty, GnRH Stimulation Test and Monitoring GnRH Analog Therapy", The Indian Journal of Pediatrics, vol. 82, No. 11 (Nov. 2015), pp. 980-982.
Neely, et al. "Leuprolide Acetate 1-Month Depot for Central Precocious Puberty: Hormonal Suppression and Recovery", International Journal of Pediatric Endocrinology, 2010, 398639, 16 pages.
Oeter et al. "Gonadotropin Secretory Dynamics During Puberty in Normal Girls and Boys", Journal of Clinical Endocrinology and Metabolism, vol. 71, No. 5 (Nov. 1990), pp. 1251-1258.
O'Hara. "Paediatric pharmacokinetics and drug doses", Australian Prescriber, vol. 39, No. 6 (Dec. 2016), pp. 208-210.
Okada. "One- and three-month release injectable microspheres of the LH-RH superagonist leuprorelin acetate", Advanced Drug Delivery Reviews, vol. 28 (Jan. 1997), pp. 43-70.
Park, et al. "Comparative in vitro release and clinical pharmacokinetics of leuprolide from Luphere 3M Depot, a 3-month release formulation of leuprolide acetate", Drug Development and Industrial Pharmacy, vol. 43, No. 3 (Mar. 2017), pp. 441-447.
Witchel, et al. "Treatment of Central Precocious Puberty: Comparison of Urinary Gonadotropin Excretion and Gonadptropin-Releasing Hormone (GnRH) Stimulation Tests in Monitoring GnRH Analog Therapy", Journal of Clinical Endocrinology and Metabolism, vol. 81, No. 4 (1996), 4 pages.

(56) References Cited

OTHER PUBLICATIONS

Wilson, et al. "Evaluation of the Buserelin Stimulation Test in Diagnosing Gonadotropin Deficiency in Males with Delayed Puberty", The Journal of Pediatrics, vol. 148, No. 1 (Jan. 2006), pp. 89-94.
Sanofi-Synthelabo Inc., ELIGARD® 45 mg Package Insert [online], (Dec. 7, 2004) [retrieved on Apr. 16, 2026]. Retrieved from the Internet :<URL:https://www.accessdata.fda.gov/drugsatfda_docs/nda/2004/021731s000_Eligard_PRNTLBL.pdf>.
Boughey, et al. "Abstract GS4-01: Impact of Breast Conservation Therapy on Local Recurrence in Patients with Multiple Ipsilateral Breast Cancer—Results from ACOSOG Z11102 (Alliance)". Cancer Res, 2023; 83 (5_Supplement): GS4-01.
AbbVie Inc., Lupron Depot Prescribing Information [online], (Jun. 2014) [retrieved on Apr. 16, 2026] Retrieved from the Internet: <URL:https://www.accessdata.fda.gov/drugsatfda_docs/label/2014/020517s036_019732s041lbl.pdf>.
AbbVie Inc., "A Study to Evaluate Safety, Efficacy, Pharmacokinetics, and Pharmacodynamics of Leuprolide Acetate 45mg 6-Month Formulation in Children With Central Precocious Puberty (CPP)" [online], NIH National Library of Medicine, submitted Oct. 2, 2018, last updated May 29, 2024, NCT03695237, 15 pages, Retrieved from the Internet:<URL:clinicaltrials.gov/ct2/show/NCT03695237?term=lupron+depot&cond=Central+Precocious+Puberty&draw=2&rank=2>.
Hospital de Niños R. Gutierrez de Buenos Aires, "Comparative Validation of the Triptorelin Test for the Diagnosis of CPP in Girls", [online] U.S. National Library of Medicine, submitted Jan. 14, 2011, last updated Jan. 6, 2021, NCT01278290, 8 pages, Retrieved from the Internet:<URL:clinicaltrials.gov/ct2/show/NCT03695237?term=lupron +depot&cond=Central+Precocious+Puberty&draw=2&rank=2>.
Klein, et al. Efficacy and safety of triptorelin 6-month formulation in patients with central precocious puberty. J Pediatr Endocrinol Metab. Nov. 1, 2016;29(11):1241-1248.
Kochar, et al. "Leuprolide vs. triptorelin: The recent trends in GnRH analogues in precocious puberty", IAIM, 2019, 6 (2): pp. 121-131.
Mayo Clinic, Precocious puberty, [online], 2017, 6 pages. Retrieved from the Internet via Wayback Machine: <URL:https://web.archive.org/web/20171110164951/https://www.mayoclinic.org/diseases-conditions/precocious-puberty/symptoms-causes/syc-203518111>, Retrieved May 8, 2021.

POLYMERIC LEUPROLIDE ACETATE FORMULATIONS

CROSS-REFERENCE TO RELATED APPLICATIONS

This application is a bypass continuation of International Application No. PCT/IB2024/056487, with an international filing date of Jul. 3, 2024, which claims priority to U.S. Provisional Application No. 63/512,016, filed Jul. 5, 2023, each of which is incorporated into this application by reference in its entirety.

BACKGROUND

This disclosure relates generally to extended release, injectable, polymeric leuprolide acetate formulations, which are easy to prepare and administer to a subject.

Leuprolide and its pharmaceutically acceptable salts, such as leuprolide acetate (LA), are gonadotropin releasing hormone (GnRH) agonists (which can also be referred to herein as a luteinizing hormone-releasing hormone (LHRH) agonists) that are useful in the treatment (which may include palliative treatment) of advanced prostate cancer, breast cancer, endometriosis, fibroids, and central precocious puberty (CPP). With continued use, LA causes pituitary desensitizing and down-regulation to affect the pituitary-gonadal axis, leading to suppressed circulating levels of luteinizing and sex hormones. In patients with advanced prostate cancer, for example, achieving circulating testosterone levels of less than or equal to 50 ng/dL (chemical castration level) is a desired pharmacological indicator of therapeutic action.

There are various products available commercially that deliver leuprolide or a pharmaceutically acceptable salt thereof into a subject for various periods of time. Most of these products require preparation and mixing steps prior to being administered to a subject. There is an ongoing, unmet need for a leuprolide acetate formulation that is even easier to prepare and administer than those currently on the market.

SUMMARY

Disclosed are pharmaceutical products for the delivery of leuprolide acetate (LA) extended release injectable compositions that are physically and chemically stable over their entire shelf life under storage conditions that are standard, or acceptable, for the pharmaceutical product, require about 30 or fewer mixing cycles to prepare the composition for administration into a subject, and which, upon injection into the subject, form an in situ depot that releases the LA over a time period from about 1 month to about 6 months.

In various embodiments, the disclosed pharmaceutical product comprises a first container comprising a polymer solution of a biodegradable polymer dissolved in a biocompatible solvent; and a second container comprising a drug solution of leuprolide acetate dissolved in the biocompatible solvent at a concentration of 20% to 45% (w/w) leuprolide acetate (e.g., 22% to 36% (w/w) leuprolide acetate); wherein the polymer and drug solutions of the first and second containers are not mixed prior to use.

The concentration of leuprolide acetate can remain at 20% to 45% (w/w) leuprolide acetate over the entire shelf life of the pharmaceutical product. For example, the concentration can remain at 20% to 45% (w/w) leuprolide acetate at 24 months or longer storage at 2 to 8° C. The concentration can also remain at 20% to 45% (w/w) leuprolide acetate at 6 months or longer storage at 25° C.

When contents of the first and second containers are mixed, the resulting composition is an extended-release composition for subcutaneous injection into a subject that upon injection into the subject, forms an in situ depot that releases the leuprolide acetate over a time period from about 1 month to about 6 months.

The biodegradable polymer can comprise one or more of the following monomers: lactide, glycolide, caprolactone, p-dioxanone, trimethylene carbonate, ethylene oxide, propylene oxide, sebacic anhydride, diketene acetals/diols, thylene oxide, 1,5-dioxepan-2-one, 1,4-dioxepan-2-one, lactic acid, glycolic acid, ethylene glycol, or any combination thereof. In some examples, the biodegradable polymer is poly(D,L-lactide-co-glycolide) (PLG), poly(D,L-lactide) (PLA), poly(lactic-glycolic acid), poly-lactic acid, or poly (D,L-lactide-co-ε-caprolactone) (PLC). In one specific example, the biodegradable polymer is poly(D,L-lactide-co-glycolide) (PLG). The molar ratio of lactide to glycolide monomers in the polymer can range from 50:50 to 95:5, e.g., 50:50, 75:25, or 85:15. The polymer solution in some example has a viscosity of 3,000 cP to 50,000 cP at 25° C.

The biocompatible solvent can be N-methyl-2-pyrrolidone (NMP), dimethyl sulfoxide (DMSO), 2-pyrrolidon, N,N-dimethylformamide, propylene carbonate (PC), caprolactam, triacetin, dimethylacetamide (DMA), benzyl benzoate (BnBzO), methyl ethyl ketone, methyl lactate, benzyl alcohol, tributyl citrate, acetyl tributyl citrate, acetyl triethyl citrate, triethyl citrate, diethylene glycol monomethyl ether, ethyl acetate, N-ethyl-2-pyrrolidone, glycofurol, polyethylene glycol, or any combination thereof.

Non-limiting examples include the following pharmaceutical products:

(i) a product where the biodegradable polymer is a PLG polymer (e.g., a PLG polymer having a 50:50 lactide to glycolide molar ratio), the biocompatible solvent is NMP; the first container is formulated to deliver 115 mg to 160 mg NMP (e.g., 120 mg to 160 mg, or 125 mg to 155 mg) and 75 mg to 90 mg of the PLG polymer, and the second container is formulated to deliver 7.5 mg leuprolide acetate and 5 mg to 40 mg NMP;

(ii) a product where the biodegradable polymer is a PLG polymer (e.g., a PLG polymer having a 75:25 lactide to glycolide molar ratio), the biocompatible solvent is NMP; the first container is formulated to deliver 90 mg to 170 mg NMP and 150 mg to 170 mg of the PLG polymer (e.g., 155 mg to 165 mg, or 155 to 160 mg), and the second container is formulated to deliver 22.5 mg leuprolide acetate and 35 mg to 105 mg NMP;

(iii) a product where the biodegradable polymer is a PLG polymer (e.g., a PLG polymer having a 75:25 lactide to glycolide molar ratio), the biocompatible solvent is NMP; the first container is formulated to deliver 80 mg to 178 mg NMP and 145 mg to 185 mg of the PLG polymer, and the second container is formulated to deliver 30 mg leuprolide acetate and 35 mg to 135 mg NMP;

(iv) a product where the biodegradable polymer is a PLG polymer (e.g., a PLG polymer having a 75:25 lactide to glycolide molar ratio), the biocompatible solvent is NMP; the first container is formulated to deliver 120 mg to 225 mg NMP and 185 mg to 235 mg of the PLG polymer, and the second container is formulated to deliver 30 mg leuprolide acetate and 35 mg to 135 mg NMP; and (v) a product where the biodegradable polymer is a PLG polymer (e.g., a PLG polymer having a 85:15 lactide to glycolide molar ratio), the biocompatible solvent is NMP; the first container is formulated to deliver 100 mg to 170 mg NMP and 145 mg to 185 mg of the PLG polymer, and the second container is formulated to deliver 45 mg leuprolide acetate and 50 mg to 95 mg NMP.

Also described is a method of reducing luteinizing hormone (LH) levels in a subject in need of LHRH reduction, comprising subcutaneously administering a pharmaceutical composition prepared by mixing the polymer and drug solutions of the first and second containers of the pharmaceutical product. In some examples, the pharmaceutical composition is prepared by mixing the polymer and drug solutions of the first and second containers using 30 or fewer mixing cycles. In further examples, the pharmaceutical composition is prepared by mixing the polymer and drug solutions of the first and second containers using 20 or fewer mixing cycles.

Administering the pharmaceutical composition can treat prostate cancer, reduce serum testosterone levels, suppress ovarian function in a subject with HR+ breast cancer, or treat central precocious puberty (CPP), among other uses. The prostate cancer can for instance be advanced prostate cancer.

The composition can be administered once per every one month, once per every three months, once per every four months, or once per every six months.

Also described is a prefilled syringe system for administration of the pharmaceutical products, wherein the first container is a first syringe comprising the polymer solution and the second container is a second syringe comprising the drug solution. The first syringe and the second syringe can be coupled together.

Also described is a kit comprising the prefilled syringe system together with instructions for mixing and administration.

Also described is an extended release composition comprising the pharmaceutical product for use in a method of reducing luteinizing hormone (LH) levels in a subject in need of LHRH reduction. Similarly, described is the use of an extended release composition comprising the pharmaceutical product in the manufacture of a medicament for use in a method of reducing luteinizing hormone (LH) levels in a subject in need of LHRH reduction.

DETAILED DESCRIPTION

Figure 1A:
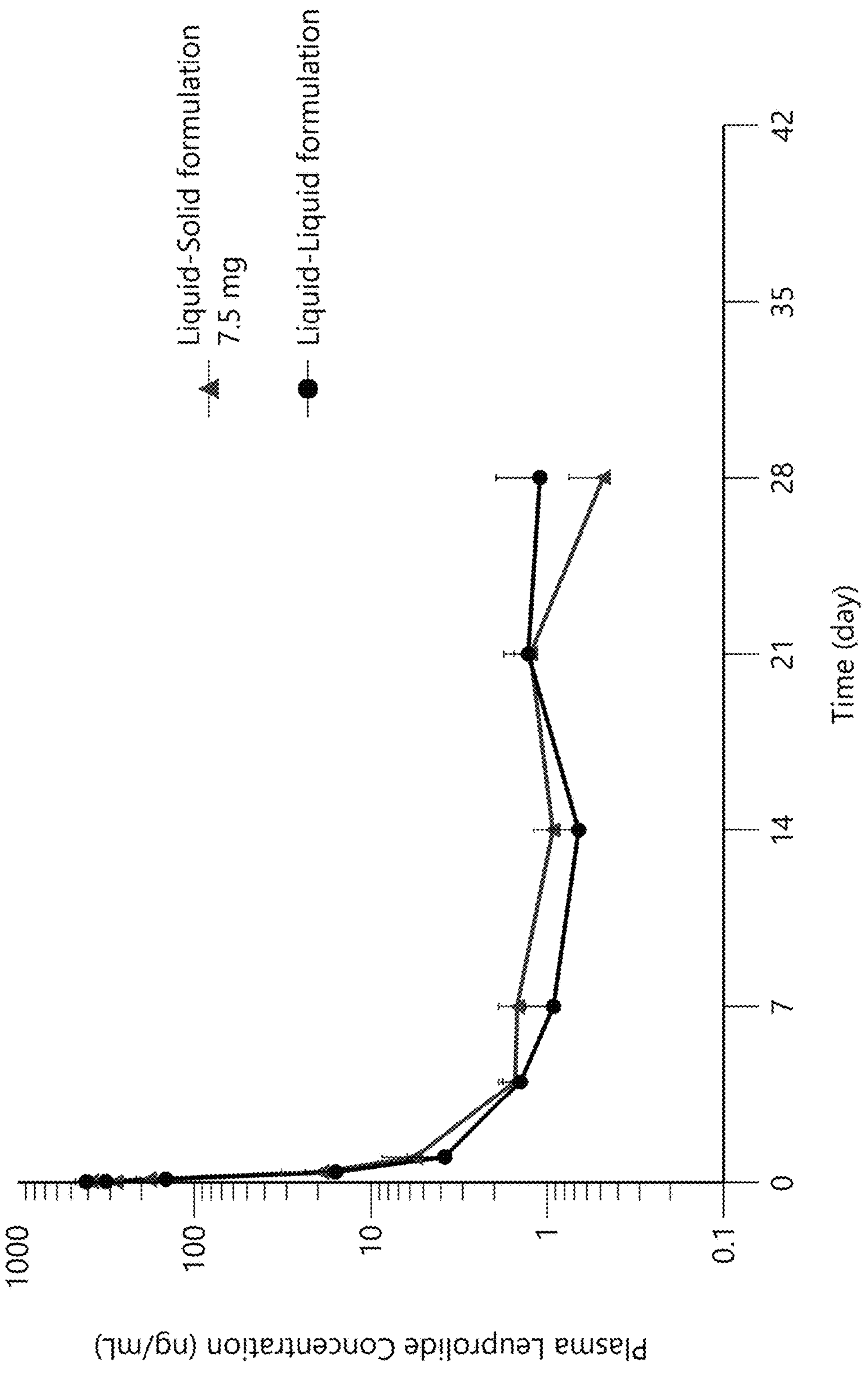
FIG. 1A shows PK study blood plasma LA concentration results comparing liquid-solid and liquid-liquid 7.5 mg formulations.
Figure 1B:
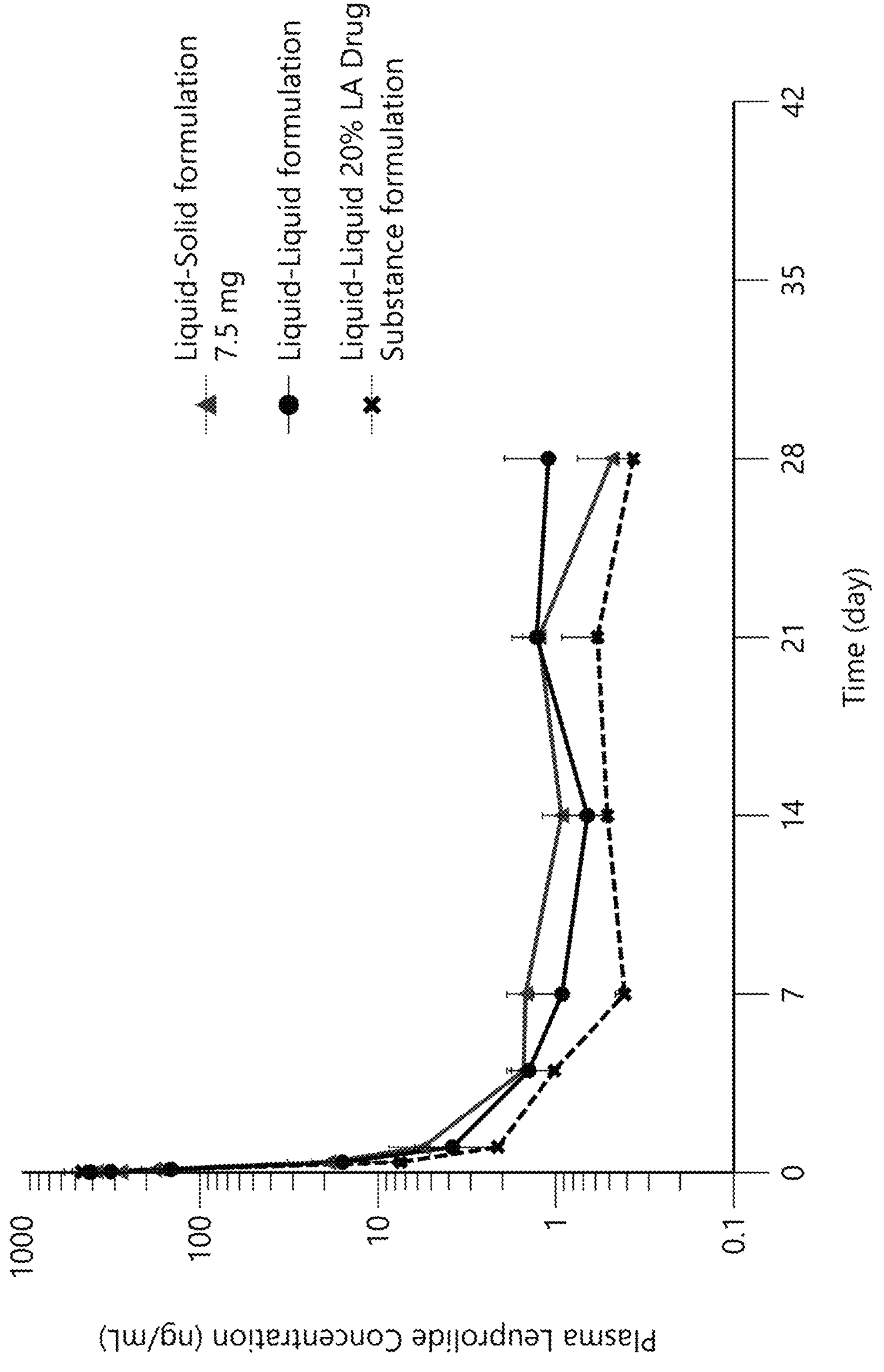
FIG. 1B shows PK study blood plasma LA concentration results comparing liquid-solid, liquid-liquid 7.5 mg, and liquid-liquid 20% LA formulations.

The present disclosure generally relates to a pharmaceutical product for the delivery of polymeric leuprolide acetate (LA) extended release injectable compositions that are physically and chemically stable over their entire shelf life under storage conditions that are standard, or acceptable, for the pharmaceutical product, require about 30 or fewer mixing cycles to prepare the composition for administration into a subject, and which, upon injection into the subject, form an in situ depot that releases the LA over a time period from about 1 month to about 6 months. The pharmaceutical product is provided as a two-container system, one container containing a polymer dissolved in a solvent, and the other container containing a drug solution of leuprolide acetate dissolved in the solvent, thus providing two liquids that are stored separately prior to mixing and administration to a subject. The resulting liquid-liquid drug product requires substantially fewer mixing cycles to achieve a homogeneous composition (e.g., a suitably uniform dispersion of the drug in polymer and solvent) suitable for administration to a subject, as compared to drug products that require mixing of a liquid polymer solution with a solid lyophilized drug (a liquid-solid formulation), for example. In the drug product of the present disclosure, it is important that the LA drug solution remain a solution over the entire shelf life of the pharmaceutical product (i.e., is physically stable), that the polymer solution be of a viscosity that allows for proper mixing of the composition prior to administration, and that the resulting composition, when mixed and administered to a subject, forms an in situ depot in the subject that releases LA over the requisite period of time, e.g., a period of time from about 1 month to about 6 months.

Producing the drug products of the present disclosure that are stable over time, as discussed above, was a challenge because, in making a drug product where both containers contain solvent (i.e., are a "liquid-liquid" drug product having one LA-solvent container and one polymer-solvent container), it was also necessary to: (1) minimize the total amount of solvent in the final composition as administered to the subject (i.e., after mixing) to be compatible with regulatory requirements for excipients; (2) ensure that mixing of the container contents to form the final composition was not more difficult (and was preferably easier) than mixing of a "liquid-solid" polymer composition that delivered the same amount of drug to a subject (i.e., mixing of lyophilized LA with a similar polymer-solvent solution), and (3) to ensure that the final composition (mixed and ready for administration) would have substantially similar drug release properties as a comparable liquid-solid composition, including releasing the drug within a subject over a targeted period of time (e.g., 1 month, 3 months, 4 months, 6 months). Accordingly, efforts were made to keep concentration of LA in the drug-solvent solution high in order to minimize the overall amount of solvent in the composition and to maintain as much solvent as possible in the polymer-solvent solution to control viscosity. However, such "liquid-liquid" drug products were prone to "gelling" or changing physical form from a liquid solution to a partial solid or gel over time during storage. While a variety of factors could have contributed to this effect, the inventors discovered that there is a range of LA concentrations in the liquid-liquid drug product that (1) maintains the mixability, injectability, and release properties of the final mixed injectable composition as compared to a liquid-solid composition having the same polymer, solvent and delivered drug amount, and (2) is physically and chemically stable as a drug product such that the LA-solvent solution remains a solution for the entire period of storage or shelf life of the drug product prior to mixing and administration.

Definitions

As used herein, the terms "active pharmaceutical ingredient," abbreviated as "API", and "drug" can be used interchangeably and generally refer to a biologically active compound that has therapeutic effects on the body. The "active pharmaceutical ingredient" may refer to an active drug, or a pharmaceutically acceptable salt of an active drug. As used herein, these terms may be used to refer to leuprolide acetate (LA).

As used herein, the term "antioxidant" refers to compounds which are used to extend the shelf-life of products by preventing or inhibiting the oxidation of active substances and excipients. An antioxidant may react with free radicals thereby blocking or inhibiting free radical chain reactions, or the antioxidant may have a lower redox potential than the active substances and excipients in the formulation. Additionally, or alternatively, a synergist antioxidant may enhance the effects of other antioxidants.

As used herein, the term "biocompatible" means "not harmful to living tissue" or "safe for injection within a human body."

As used herein, the term "biodegradable" refers to any material that is converted, breaks down, or degrades, under physiological conditions into innocuous or natural byproducts, such as (but not limited to) water, gas, biomass, and/or organic salts, without regard to any specific degradation mechanism or process.

As used herein, the terms "molecular weight" and "average molecular weight," unless otherwise specified, refer to a weight-average molecular weight as measured by a conventional gel permeation chromatography (GPC) instrument (such as an Agilent 1260 Infinity Quaternary LC with Agilent G1362A Refractive Index Detector) utilizing polystyrene standards and tetrahydrofuran (THF) as the solvent.

As used herein, the terms "patient" and "subject" are interchangeable and generally refer to an animal or a human to which a composition disclosed herein is administered or is to be administered.

As used herein, the term "pharmaceutically acceptable salt" refers to a salt of a compound, which possesses the desired pharmacological activity of the parent compound. Such salts include, but are not limited to: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, lauric acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, pamoic acid, palmitic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like. By way of example, leuprolide acetate is a pharmaceutically acceptable salt of leuprolide.

As used herein, the term "solvent" refers to a liquid that dissolves a solid or liquid solute, or into which a solid or liquid substance may be suspended or dispersed. Solvents may form a solution when provided in relatively large quantities. One or more solvents may form a suspension when provided in relatively small quantities and/or when used as a co-solvent or additive.

As used herein, the term "co-solvent" refers to a substance added to a solvent to increase or modify the solubility of a solute in the solvent.

As used herein, the term "solubilizer" refers to a compound that increases the solubility of another substance.

As used herein, the term "surfactant" refers to a compound that lowers the surface tension between two liquids, between a gas and a liquid, or between a liquid and a solid. For example, a surfactant can act as a wetting agent, which aids in dispersing an active pharmaceutical ingredient in a liquid vehicle, or as a solubilizer under some circumstances.

As used herein, the term "therapeutically effective amount" means the amount of a compound or drug product that, when administered to a patient for treating a disease and/or treating or preventing one or more symptoms of a disease, is sufficient to affect such treatment or prevention for the disease. The "therapeutically effective amount" can vary depending on, for example, the compound or drug product, disease progression, the disease or condition to be treated, whether the therapy is an adjuvant therapy or a primary or curative therapy, and/or the age, weight, etc., of the patient to be treated. By way of a non-limiting example, a therapeutically effective amount of the pharmaceutical products disclosed herein, can include an amount effective to: (1) treat a disease or condition (e.g., including as a palliative therapy) including, but not limited to, hormone-related cancers and other conditions, including hormone-related prostate cancer (including advanced prostate cancer), hormone-related mammary (breast) cancer (including hormone receptor positive (HR+) mammary cancer), hormone-related endometrial cancer, hormone-related ovarian cancer, hormone-related cervical cancer, endometriosis, fibroids, and central precocious puberty (CPP); (2) reducing the levels in a subject of various hormones by GnRH pathways (testosterone, estrogen/estradiol, luteinizing hormone (LH), follicle stimulating hormone (FSH), etc.), (3) suppressing functions associated with hormones in the GnRH pathways, such as suppressing ovarian function in a subject with HR+ breast cancer; and (4) blocking or suppression hormones in the GnRH pathway for other purposes, such as to prevent or delay puberty in a transgender individual.

As used herein, "area under the curve" or "AUC" in pharmacokinetics, is the area under a plot of the concentration of a drug in the blood plasma as a function of time, and reflects the actual body exposure to a drug after administration of a dose of the drug. AUC is dependent on the rate of elimination of the drug from the body and the dose administered.

As used herein, the terms "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

As used herein, the term "depot" refers to the composition/formulation disclosed herein where, upon contact with an aqueous environment (e.g., upon administration to a subject and contact with a bodily fluid), the solvent(s) dissipates, creating a polymer-drug monolithic reservoir from which the drug (LA) is released over an extended period of time.

As used herein, reference to "shelf life" of a drug product refers to the time period during which the drug product is known to remain stable, which means it retains its strength, quality, and purity when it is stored according to, for example, its labeled storage conditions. For drug products approved by a regulatory body, such as the U.S. Food & Drug Administration (USFDA), shelf life may also be referred to by way of an "expiration date." Shelf life is typically referenced with respect to storage conditions including a maximum time period (typically referenced in months) and a temperature range.

Unless otherwise specified, all ratios between monomers in a copolymer disclosed herein are molar ratios.

Unless otherwise specified, various amounts of API, biodegradable polymer, and solvents and co-solvents are reported in weight percentages of the solvent system, solvent system and biodegradable polymer, or pharmaceutical composition.

Every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include both terminal values as well as each and every narrower numerical range that falls within such broader numerical range, as if such narrower numerical ranges were all expressly written herein. By way of example, the phrase from about 2 to about 4 includes the whole number and/or integer ranges from about 2 to about 3, from about 3 to about 4 and each possible range based on real (e.g., irrational and/or rational) numbers, such as from about 2.1 to about 4.9, from about 2.1 to about 3.4, and so on.

Reference will now be made in detail to particular embodiments of pharmaceutical products, compositions, compounds, formulations, and methods. The disclosed embodiments are not intended to be limiting of the claims.

LA is an LHRH agonist analog that is useful in the treatment, which may be palliative treatment, of hormone-related cancers and other conditions, including hormone-related prostate cancer, hormone-related mammary (breast) cancer, hormone-related endometrial cancer, hormone-related ovarian cancer, hormone-related cervical cancer, endometriosis, fibroids, and central precocious puberty (CPP) and other conditions or non-disease uses. With continued use, LA causes pituitary desensitizing and down-regulation to affect the pituitary-gonodal axis, leading to suppressed circulating levels of luteinizing and sex hormones.

Disclosed herein is an extended release, injectable pharmaceutical product/composition/formulation that comprises LA in a polymer-based drug delivery system. The pharmaceutical product comprises a first container comprising biodegradable polymer in a biocompatible solvent; and a second container comprising a drug solution comprising LA dissolved in the biocompatible solvent, where the drug solution remains a solution, and where the drug solution concentration is, and remains, less than 45% w/w LA, or less than 44% w/w LA, or less than 43% w/w LA, or less than 42% w/w LA, or less than 41% w/w LA, or less than 40% w/w LA in the biocompatible solvent, over the entire shelf life of the product. Also disclosed is a pharmaceutical product that comprises a first container comprising biodegradable polymer in a biocompatible solvent; and a second container comprising a drug solution comprising LA dissolved in the biocompatible solvent, where the drug solution remains a solution, and where the drug solution concentration is, and remains, no more than 44% w/w LA, 43% w/w LA, 42% w/w LA, 41% w/w LA, or 40% w/w LA in the biocompatible solvent, over the entire shelf life of the product. In embodiments, the second container of a pharmaceutical product of the disclosure comprises a drug solution comprising LA dissolved in the biocompatible solvent, where the drug solution concentration at the time of manufacture of the pharmaceutical product is no more than about 42% w/w LA, about 41% w/w LA, about 40% w/w LA, about 39% w/w LA, about 38% w/w LA, about 37% w/w LA, about 36% w/w LA, or about 35% w/w LA in the biocompatible solvent. In embodiments, the second container of a pharmaceutical product of the disclosure comprises a drug solution comprising LA dissolved in the biocompatible solvent, where the drug solution concentration at the time of manufacture of the pharmaceutical product is no more than about 35 to about 40% w/w LA in the biocompatible solvent. In embodiments, the second container of a pharmaceutical product of the disclosure comprises a drug solution comprising LA dissolved in the biocompatible solvent, where the drug solution concentration at the time of manufacture of the pharmaceutical product is no more than about 35% w/w LA in the biocompatible solvent.

In some embodiments, the drug solution is at a concentration of about 20% to about 45% (w/w) leuprolide acetate. In some embodiments, the drug solution is at a concentration of about 22% to about 36% (w/w). In some embodiments, the concentration of the drug solution remains at 20% to 45% (w/w) leuprolide acetate over the entire shelf life of the pharmaceutical product. In some embodiments, the concentration of the drug solution remains at 20% to 45% (w/w) leuprolide acetate at 24 months or longer storage at 2 to 8° C. In some embodiments, the concentration of the drug solution remains at 20% to 45% (w/w) leuprolide acetate at 6 months or longer storage at 25° C. In some embodiments, the concentration of the drug solution remains at 22% to 36% (w/w) leuprolide acetate over the entire shelf life of the pharmaceutical product. In some embodiments, the concentration of the drug solution remains at 22% to 36% (w/w) leuprolide acetate at 24 months or longer storage at 2 to 8° C. In some embodiments, the concentration of the drug solution remains at 22% to 36% (w/w) leuprolide acetate at 6 months or longer storage at 25° C.

In any of the above embodiments, when the contents of the first and second containers are mixed, the resulting composition is an extended-release composition for subcutaneous injection into a subject that upon injection into the subject, forms an in situ depot that releases the LA over a time period from about 1 month to about 6 months.

The amount of LA in the second container refers to the amount, by weight, of the leuprolide salt, leuprolide acetate, in relation to the amount of solvent, by weight, contained within the second container. The amount of LA referenced in the second container is not to be confused with a calculation of the amount of leuprolide (free-base) or with the amount of an LA drug substance (such as produced by an API manufacturer) which may contain additional small amounts of impurities arising from the API manufacturing process. For example, when LA is provided at 45% in a solution, the conversion factor used to calculate the equivalent amount of leuprolide (free-base) is typically 1.078, resulting in a equivalent leuprolide free base content of about 41.74% (45/1.078=41.74). For the same amount of 45% LA, the LA drug substance provided by the API manufacturer will typically be higher than 45% and will vary from lot to lot of API drug substance, since the LA drug substance typically contains small amounts of impurities from the manufacturing process that may vary from manufacturer to manufacturer and from lot to lot of API.

The resultant extended-release composition is a flowable solution/suspension where, upon delivery (i.e., injection) into an aqueous environment (e.g., the body of a human), the water-miscible solvent exchanges with surrounding aqueous body fluids, which results in the formation of a solid, semi-solid, or liquid polymer-drug depot in situ upon dissipation of the solvent, that acts as a drug reservoir for extended release of the drug (i.e. release of the drug over an extended period of time).

The pharmaceutical products disclosed herein provide sustained or extended release of LA for one month or longer, depending on the formulation of the product, when injected via subcutaneous injection. The pharmaceutical products suitable for use in the methods of this disclosure, which, when prepared for administration, may also be referred to as pharmaceutical compositions or formulations, extended-release products, compositions or formulations, or controlled release products, compositions or formulations, provide a biodegradable or bioerodible microporous in situ formed depot of LA in a subject, from which the LA is released over a period of one month to about 6 months. The product can be supplied in any configuration in which the contents of the first container are separated from the contents of the second container during storage of the product (prior to administration to a subject), and can be readily mixed and then injected to a subject in need of the resulting composition. For example, a suitable configuration includes a prefilled two-syringe system that may be pre-connected to facilitate mixing, or in a dual-chambered mixing syringe, or another other configuration. This product has advantages of providing a product that, due to the liquid-liquid format of the pharmaceutical product, substantially reduces mixing cycles as compared to liquid-solid pharmaceutical products having comparable polymer-solvent delivery systems.

After mixing of the pharmaceutical products of the disclosure, the resulting composition is administered by injection using a syringe and needle or other suitable injection device to a subject, whereby LA is released from the polymer depot over a period of at least about 1 month or longer, at least about 1.5 months or longer, at least about 2 months or longer, at least about 2.5 months or longer, at least about 3 months or longer, at least about 3.5 months or longer, at least about 4 months or longer, at least about 4.5 months or longer, at least about 5 months or longer, or at least about 6 months or longer. The duration of release from the depot can depend on one or a number of factors including, for example, the nature of the biodegradable polymer, the composition and molecular weight of the biodegradable polymer, the solvent, amounts of the components in the product/composition, combinations of any of the foregoing, or other factors.

Active Pharmaceutical Ingredient (API)/Drug Solution (DS)

The product/compositions/formulations disclosed herein comprise LA (i.e., the API) in polymer-based drug delivery system.

Generally, the disclosed products comprise a first container comprising biodegradable polymer dissolved in a biocompatible solvent; and a second container comprising a drug solution comprising LA dissolved in the biocompatible solvent, wherein, for the entire shelf life of the product, the drug solution remains a solution and the drug solution concentration is less than 45% w/w LA in the biocompatible solvent. In other words, regardless of the starting drug solution concentration when the pharmaceutical product is first produced or manufactured, over the full shelf life of the product, when solvent may, depending on the container configuration and/or materials, leak or evaporate in small quantities, the drug solution concentration must always be less than 45% w/w LA in the biocompatible solvent. In aspects of the disclosure, for the entire shelf life of the product, the drug solution remains a solution and the drug solution concentration is less than 44% w/w LA, or less than 43% w/w LA, or less than 42% w/w LA, or less than 41% w/w LA, or less than 40% w/w LA, less than 39% w/w LA, less than 38% w/w LA, less than 37% w/w LA, or less than 36% w/w LA, in the biocompatible solvent. In some embodiments, the drug solution concentration, at any or all times in the life of the product (e.g., at any or all times from when the product is first produced or manufactured through expiration, or end of shelf life, of the product), is 20% to 45% w/w LA or 22% to 36% w/w LA, e.g., 20% LA, 21% LA, 22% LA, 23% LA, 24% LA, 25% LA, 26% LA, 27% LA, 28% LA, 29% LA, 30% LA, 31% LA, 32% LA, 33% LA, 34% LA, 35% LA, 36% LA, 37% LA, 38% LA, 39% LA, 40% LA, 41% LA, 42% LA, 43% LA, 44% LA, or 45% LA.

In embodiments, the disclosed products comprise a first container comprising biodegradable polymer dissolved in a biocompatible solvent; and a second container comprising a drug solution comprising LA dissolved in the biocompatible solvent, wherein, for the entire shelf life of the product, the drug solution remains a solution and the drug solution concentration is no more than 45% w/w/LA, 44% w/w LA, 43% w/w LA, 42% w/w LA, 41% w/w LA, 40% w/w LA, 39% w/w LA, 38% w/w LA, 37% w/w LA, 36% w/w LA, 35% w/w LA, in the biocompatible solvent. Similarly to the discussion above, in other words, regardless of the starting drug solution concentration when the pharmaceutical product is first produced or manufactured, over the full shelf life of the product, when solvent may, depending on the container configuration and/or materials, leak or evaporate in small quantities, the drug solution concentration may always be no more than 45% or 44% w/w LA in the biocompatible solvent.

Accordingly, in any of the above embodiments, in aspects of the disclosure, the drug solution concentration at the time of manufacture or production of the pharmaceutical product (i.e., the targeted drug solution concentration, which may be a range according to product specifications) is no more than about 45% w/w LA, about 44% w/w LA, about 43% w/w LA, about 42% w/w LA, about 41% w/w LA, about 40% w/w LA, about 39% w/w LA, about 38% w/w LA, about 37% w/w LA, about 36% w/w LA, or about 35% w/w LA in the biocompatible solvent. In aspects, the drug solution concentration at the time of manufacture or production of the pharmaceutical product is no more than about 20% to about 45% w/w LA in the biocompatible solvent, or no more than about 20% to about 40% w/w LA, no more than about 22% to about 36% w/w LA. In further aspects, the drug solution concentration at the time of manufacture or production of the pharmaceutical product is no more than about 22% to about 39% w/w LA, no more than about 22% to about 38% w/w LA, no more than about 22% to about 37% w/w LA, or no more than about 22% to about 36% w/w LA. In aspects, the drug solution concentration of the pharmaceutical product when the pharmaceutical product is manufactured, is between about 5% to about 45% w/w LA in the biocompatible solvent, between about 10% to about 45% w/w LA in the biocompatible solvent, between about 20% to about 45% w/w LA in the biocompatible solvent, or between about 20% to about 42% w/w LA in the biocompatible solvent, or between about 22% to about 36% w/w LA in the biocompatible solvent. In some embodiments, the drug solution concentration at the time of manufacture or production of the pharmaceutical product is less than about 45% w/w LA, less than about 44% w/w LA, less than about 43% w/w LA, less than about 42% w/w LA in the biocompatible solvent, or less than about 41% w/w LA in the biocompatible solvent, or less than about 40% w/w LA in the biocompatible solvent, or less than about 39% w/w LA in the biocompatible solvent, or less than about 38% w/w LA in the biocompatible solvent, or less than about 37% w/w LA in the biocompatible solvent, or less than about 36% w/w LA in the biocompatible solvent, or less than about 35% w/w LA in the biocompatible solvent, or less than about 30% w/w LA in the biocompatible solvent, or less than about 30% in the biocompatible solvent, or less than about 25% w/w in the biocompatible solvent.

The drug solution concentration at the time of manufacture or production of the pharmaceutical product (i.e., the targeted drug solution concentration) can vary and may range from about 5% to about 45% LA by weight in the biocompatible solvent, including any whole number percent to any other whole number percent within the range of from about 5 percent to about 45 percent by weight. Regardless of the drug solution concentration at the time of manufacture or production of the pharmaceutical product, the drug solution concentration remains a solution and is less than 45% w/w LA in the biocompatible solvent over the shelf life of the pharmaceutical product, and/or the drug solution concentration remains a solution and is no more than 45% or 44% w/w LA in the biocompatible solvent over the shelf life of the pharmaceutical product.

In embodiments of the disclosure, the shelf life of the pharmaceutical product is about 12 months, about 18 months, about 24 months, about 30 months, about 36 months, about 42 months, about 48 months, about 54 months or about 60 months storage at 2-8° C. In embodiments, the shelf life of the pharmaceutical product is about 12 months, about 18 months, about 24 months, about 30 months, about 36 months, about 42 months, about 48 months, about 54 months or about 60 months storage at room temperature. In embodiments, the shelf life of the pharmaceutical product is about 6 months, about 12 months, about 18 months, about 24 months, about 30 months, about 36 months, about 42 months, about 48 months, about 54 months or about 60 months storage at up to 25° C. In other embodiments, the drug solution concentration is less than 45% w/w/LA, less than 44%, less than 43%, less than 42%, less than 41%, less than 40%, less than 39%, less than 38%, less than 37%, less than 36% or less than 35%, w/w LA in the biocompatible solvent at about 24 months storage at 2-8° C. In embodiments, the drug solution concentration is no more than 44%, or no more than 43%, or no more than 42%, or no more than 41%, or no more than 40%, or no more than 39%, or no more than 38%, or no more than 37%, or no more than 36%, or no more than 35%, w/w LA in the biocompatible solvent at about 24 months storage at 2-8° C. In still other embodiments, the drug solution concentration is less than 45% w/w/LA, less than 44%, less than 43%, less than 42%, less than 41%, less than 40%, less than 39%, less than 38%, less than 37%, less than 36% or less than 35%, w/w LA in the biocompatible solvent, at about 6 months storage at 25° C. In still other embodiments, the drug solution concentration is no more than 44%, or no more than 43%, or no more than 42%, or no more than 41%, or no more than 40%, or no more than 39%, or no more than 38%, or no more than 37%, or no more than 36%, or no more than 35%, w/w LA in the biocompatible solvent at about 6 months storage at 25° C.

In other embodiments, the drug solution concentration at about 24 months storage at 2-8° C. is 20% to about 45% w/w LA in the biocompatible solvent, or no more than about 20% to about 40% w/w LA, or no more than about 22% to about 36% w/w LA. In further aspects, the drug solution concentration at about 24 months storage at 2-8° C. is no more than about 22% to about 39% w/w LA, or no more than about 22% to about 38% w/w LA, or no more than about 22% to about 37% w/w LA, or no more than about 22% to about 36% w/w LA. In other embodiments, the drug solution concentration at about 6 months storage at 25° C. is 20% to about 45% w/w LA in the biocompatible solvent, or no more than about 20% to about 40% w/w LA, or no more than about 22% to about 36% w/w LA. In further aspects, the drug solution concentration at about 6 months storage at 25° C. is no more than about 22% to about 39% w/w LA, or no more than about 22% to about 38% w/w LA, or no more than about 22% to about 37% w/w LA, or no more than about 22% to about 36% w/w LA.

Biocompatible/Biodegradable Polymers

Polymers suitable for use in the disclosed products/compositions include polymers, copolymers, di-block or tri-block copolymers, and/or terpolymers formed of repeating units, which can be linear, branched, grafted and/or star-shaped. Further, the polymers can comprise monomers, such as lactide, glycolide, caprolactone, p-dioxanone, trimethylene carbonate, thylene oxide, 1,5-dioxepan-2-one, 1,4-dioxepan-2-one, ethylene oxide, propylene oxide, sebacic anhydride, diketene acetals/diols, lactic acid, glycolic acid, ethylene glycol, and combinations thereof.

Biodegradable polymers suitable for use with the disclosed products/compositions include, but are not limited to, polylactic acid, polyglycolic acid, polylactide (D-lactide, L-lactide), poly(D,L-lactide) (PLA), polyglycolide, polycaprolactones, poly(D,L-lactide-co-glycolide) (PLG), poly (D,L-lactide-co-ε-caprolactone) (PLC), polyanhydrides, polyamides, polyurethanes, polyesteramides, polyorthoesters, polydioxanones, polyacetals, polyketals, polycarbonates, polyphosphazenes, polyhydroxybutyrates, polyhydroxyvalerates, polyalkylene oxalates, polyalkylene succinates, poly(malic acid), polyglutamic acids, poly(alkyl cyanoacrylates) polyethylene glycol, hyaluronic acid, alginate, collagen, chitin and chitosan, and combinations or mixtures of the above materials. In preferred embodiments, the biodegradable polymer is PLG, PLA or PLC.

In some embodiments, the biodegradable polymer may be a copolymer of two monomers having a molar ratio of any two whole numbers X to Y, such that the sum of X and Y is 100. In some embodiments, the biodegradable polymer may be a copolymer of two monomers having a molar ratio of any two whole numbers X to Y, where X and Y are each at least about 10 and no more than about 90, such that the sum of X and Y is 100, e.g., a copolymer comprising a 10:90 to 90:10 molar ratio of X:Y. In some embodiments, X and Y may be at least about 15 to no more than about 85 such that the sum of X and Y is 100, e.g., a copolymer comprising a 15:85 to 85:15 molar ratio of X:Y. In some embodiments, X and Y may be at least about 25 to no more than about 75 such that the sum of X and Y is 100, e.g., a copolymer comprising a 25:75 to 75:25 molar ratio of X:Y. In some embodiments, both X and Y may be about 50, e.g., a copolymer comprising a 50:50 molar ratio of X:Y.

In some embodiments, the biodegradable polymer is a copolymer comprising (a) D,L-lactide, D-lactide, L-lactide or glycolide monomers and (b) caprolactone monomers. In some embodiments, the biodegradable polymer is a copolymer comprising lactide, preferably D,L-lactide, and caprolactone monomers. In some embodiments, the biodegradable polymer is poly(D,L-lactide-co-ε-caprolactone) (PLC). In one aspect the PLC comprises at least one carboxylic acid end group. In one aspect, the PLC is a carboxylic acid-initiated PLC. In still another aspect, the carboxylic acid is glycolic acid or lactic acid. In some embodiments, the polymer is a copolymer comprising a molar ratio of lactide (or glycolide) to ε-caprolactone ranging from about 10:90 to about 90:10, from about 20:80 to about 80:20, from about 25:75 to about 75:25, or from about 30:70 to about 70:30. In one aspect, the ratio of lactide (or glycolide) to ε-caprolactone is from about 25:75 to about 75:25. In one aspect, the ratio of lactide (or glycolide) to ε-caprolactone is from about 50:50 to about 75:25. In one aspect, the ratio of lactide (or glycolide) to ε-caprolactone is about 50:50. In still another aspect, the ratio of lactide (or glycolide) to ε-caprolactone is about 75:25. In one aspect, the biodegradable polymer is acid-initiated 75:25 poly(D,L-lactide-co-8-caprolactone). In aspects, the biodegradable polymers of the disclosure can be made using any suitable method, including, but not limited to ring opening or condensation polymerization.

In some embodiments, the biodegradable polymer comprises at least one carboxylic acid end group, at least one hydroxyl end group, or at least one hydroxy end group and is substantially free of terminal carboxy end groups as discussed in more detail below.

In some embodiments, the biodegradable polymer is a copolymer comprising (a) D,L-lactide, D-lactide, L-lactide or glycolide monomers and (b) trimethylene carbonate (TMC) monomers. In some embodiments, the biodegradable polymer is a copolymer comprising lactide, preferably D,L-lactide, and TMC monomers. In some embodiments, the biodegradable polymer is a copolymer comprising a molar ratio of lactide (or glycolide) to TMC ranging from about 10:90 to about 90:10, from about 20:80 to about 80:20, from about 25:75 to about 75:25, or from about 30:70 to about 70:30. In one aspect, the ratio of lactide (or glycolide) to TMC is from about 25:75 to about 75:25. In one aspect, the ratio of lactide (or glycolide) to TMC is about 50:50. In still another aspect, the ratio of lactide (or glycolide) to TMC is about 75:25.

In some embodiments, the biodegradable polymer is a copolymer comprising (a) D,L-lactide, D-lactide, or L-lactide monomers and (b) glycolide monomers. In some embodiments, the biodegradable polymer is poly(DL-lactide-co-glycolide) (PLG). In one aspect the PLG comprises at least one carboxylic acid end group. In one aspect, the PLG is a core-diol-initiated PLG. In one aspect, the core diol is 1,6-hexane diol. In one aspect, the PLG was initiated with an uncapped polyethylene glycol (PEG). In still another aspect, the PLG is a mono functional alcohol-initiated PLG. In one aspect, the mono functional alcohol is dodecanol. In another aspect, the PLG was initiated with a mono-capped PEG (mPEG). In a non-limiting example, the PLG has a molar ratio of lactide monomers to glycolide monomers from about 50:50 to about 90:10. In one aspect, the PLG has a molar ratio of lactide to glycolide monomers from about 45:55 to about 99:1. In some instances, the PLG copolymer may comprise a lactide to glycolide monomer molar ratio from about 50:50 to about 90:10, from about 50:50 to about 80:20, from about 50:50 to about 70:30, or from about 50:50 to about 75:25. In one aspect the molar ratio of lactide monomers to glycolide monomers is 50:50, 75:25, or 85:15. In one aspect, the biodegradable polymer is acid-initiated 50:50 poly(D,L-lactide-co-glycolide). In another aspect, the biodegradable polymer is 1,6-hexane diol initiated 75:25 poly(D,L-lactide-co-glycolide). In yet another aspect, the biodegradable polymer is 1,6-hexane diol initiated 85:15 poly(D,L-lactide-co-glycolide). In yet a further aspect, the biodegradable polymer is dodecanol-initiated poly(D,L-lactide).

In one embodiment, the PLG comprises at least one carboxylic acid end group. Further, the biodegradable polymer is acid-initiated 50:50 PLG and is present in the polymer solution at about 35 wt %, 35.5 wt %, 36 wt %, 36.5 wt %, 37 wt %, 37.5 wt %, 38 wt %, 38.5 wt %, 39 wt %, or about 35 to 39 wt %. In one aspect, biodegradable polymer in the polymer solution is acid-initiated 50:50 PLG, and the polymer solution contributes from (is formulated to deliver) about 80 to 85 mg of biodegradable polymer to the final pharmaceutical composition as delivered to a subject (i.e., post mixing of the first and second containers). In one aspect, biodegradable polymer in the polymer solution is acid-initiated 50:50 PLG, and the polymer solution contributes about 82.5 mg biodegradable polymer to the final pharmaceutical composition as delivered to a subject.

In yet another embodiment, the PLG comprises at least one hydroxyl end group. In one aspect, the PLG is a core-diol-initiated PLG. In one aspect, the core diol is 1,6-hexane diol. In still another aspect, the biodegradable polymer is 1,6-hexane-diol-initiated 75:25 PLG and is present in the polymer solution at about 48 wt %, 48.5 wt %, 49 wt %, 49.5 wt %, 50 wt %, 50.5 wt %, 51 wt %, 51.5 wt %, 52 wt %, 52.5 wt %, 53 wt %, 53.5 wt %, 54 wt %, 54.5 wt %, 55 wt %, 55.5 wt %, 56 wt %, 56.5 wt %, 57 wt %, 57.5 wt %, 58 wt %, 58.5, wt %, 59 wt %, 59.5 wt %, 60 wt %, 60.5 wt %, 61 wt %, 61.5 wt %, 62 wt %, 62.5 wt %, 63 wt %, 63.5 wt %, 64 wt %, 64.5 wt %, 65 wt %, 65.5 wt %, 66 wt %, 66.5 wt %, 67 wt %, 67.5 wt %, or 68 wt %.

In one aspect, the biodegradable polymer is 1,6-hexane-diol-initiated 75:25 PLG and is present in the polymer solution at about 48.5 to 67 wt %. In one aspect, the biodegradable polymer in the polymer solution is 1,6-hexane-diol-initiated 75:25 PLG, and the polymer solution contributes from about 155 to 160 mg or about 158.6 mg biodegradable polymer to the final extended release composition as delivered to a subject (i.e., post mixing of the first and second containers).

In one aspect, the biodegradable polymer in the polymer solution is 1,6-hexane-diol-initiated 75:25 PLG, and the polymer solution contributes about 166 mg biodegradable polymer to the final pharmaceutical composition as delivered to a subject. In one aspect, the biodegradable polymer in the polymer solution is 1,6-hexane-diol-initiated 75:25 PLG, and the polymer solution contributes about 205 to 215 mg biodegradable polymer to the final pharmaceutical composition as delivered to a subject. In one aspect, the biodegradable polymer in the polymer solution is 1,6-hexane-diol-initiated 75:25 PLG, and the polymer solution contributes about 211.5 mg biodegradable polymer to the final pharmaceutical composition as delivered to a subject.

In yet another aspect, the biodegradable polymer is 1,6-hexane-diol-initiated 85:15 PLG and is present in the polymer solution at about 50 wt %, 50.5 wt %, 51 wt %, 51.5 wt %, 52 wt %, 52.5 wt % 53 wt %, 53.5 wt % 54 wt %, 54.5 wt % 55 wt % 55.5 wt % 56 wt % 56.5 wt %, 57 wt % 57.5 wt %, 58 wt % 58.5 wt %, 59 wt % 59.5 wt %, 60 wt 60.5 wt %, or 61 wt % In one aspect, the biodegradable polymer is 1,6-hexane-diol-initiated 85:15 PLG and is present in the polymer solution at about 50 to 60 wt %. In a preferred aspect, the biodegradable polymer is 1,6-hexane-diol-initiated 85:15 PLG and is present in the polymer solution at about 55 wt %. In one aspect, the biodegradable polymer in the polymer solution is 1,6-hexane-diol-initiated 85:15 PLG, and the polymer solution contributes from about 160 to 170 mg biodegradable polymer to the final pharmaceutical composition as delivered to a subject (i.e., post mixing of the first and second containers). In one aspect, the biodegradable polymer in the polymer solution is 1,6-hexane-diol-initiated 85:15 PLG, and the polymer solution contributes 165 mg biodegradable polymer to the final pharmaceutical composition as delivered to a subject.

In some embodiments, the biodegradable polymer is poly(D,L-lactide) (PLA). In one aspect, the (PLA) comprises at least one carboxylic acid end group.

Further non-limiting examples of suitable polymers include biodegradable polymers comprising a copolymer with lactide (including D,L-lactide, D-lactide, and/or L-lactide) and/or glycolide residues, wherein the molar percentage of the lactide and/or glycolide residues make up greater than about 5% and less than about 95% of the polymer. In some embodiments, the lactide and/or glycolide monomers make up at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of total monomers of the copolymer. Other non-limiting examples of suitable polymers of the disclosure include biodegradable polymers comprising a copolymer with caprolactone and/or TMC residues, wherein the caprolactone and/or trimethylene carbonate residues make up in an amount greater than about 5% and less than about 95% of the polymer. In some embodiments, the caprolactone and/or TMC monomers make up at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of total monomers of the copolymer.

In some embodiments, the biodegradable polymer may be formed using an initiator selected to provide a desired structure or functionality to the polymer in the form of a particular polymer block structure or end group structure which is introduced and/or incorporated into/onto the biodegradable polymer. By way of another non-limiting example, the polymer may be formed using an organic acid (e.g., a hydroxy acid such as, for instance, glycolic acid) as the initiator which may result in the formation of a polymer comprising at least one carboxylic acid end group. By way of another non-limiting example, the polymer may be formed using a monofunctional alcohol (e.g., dodecanol, or monomethoxy endcapped monofunctional polyethylene glycols (PEGs)) as the initiator which may result in the formation of a polymer comprising at least one hydroxy end group. By way of a further non-limiting example, the polymer may be formed using a diol (e.g., hexanediol, PEG300, PEG400, PEG600) as the initiator which may result in the formation of a polymer comprising at least one hydroxy end group and that is also substantially free of terminal carboxy end groups. In some embodiments, the biodegradable polymer may be formed using an initiator selected to provide a desired structure, and in particular a desired polymer block structure or end group structure, to the biodegradable polymer. By way of non-limiting example, the polymer may be formed using a low-molecular weight PEG (e.g., the above-mentioned PEG300, PEG400 or PEG600) as an initiator, which may result in the formation of a block copolymer comprising a low-molecular weight PEG block. By way of non-limiting example, block A may comprise first monomers selected from D,L-lactide, D-lactide, or L-lactide, and second monomers selected from glycolide, ε-caprolactone, or trimethylene carbonate. Block B comprises a low-molecular weight polyethylene glycol (PEG). The blocks may be arranged in any number or order (e.g., as a di-block copolymer A-B, or a tri-block copolymer A-B-A or B-A-B). Such polymers are formed by initiation of the first and second monomers with a low-molecular weight PEG initiator. As provided for above, in some embodiments, the biodegradable polymer comprises at least one carboxylic acid end group, at least one hydroxyl end group, or at least one hydroxy end group and is substantially free of terminal carboxy end groups.

In some embodiments, biodegradable polymers suitable for use in the products/compositions according to the present disclosure may, generally, comprise a weight average molecular weight ranging from about 1 kDa and about 100 kDa. In some embodiments, the biodegradable polymer may comprise a weight average molecular weight ranging from about 1 kDa to about 5 kDa, from about 1 kDa to about 10 kDa, from about 1 kDa to about 15 kDa, from about 1 kDa to about 20 kDa, from about 1 kDa to about 25 kDa, from about 1 kDa to about 30 kDa, from about 1 kDa to about 40 kDa, from about 1 kDa to about 45 kDa, from about 1 kDa to about 50 kDa, from about 1 kDa to about 60 kDa, from about 1 kDa to about 70 kDa, from about 1 kDa to about 80 kDa, from about 1 kDa to about 90 kDa, from about 1 kDa to about 100 kDa, or any value to any other value, in whole number increments, from about 1 kDa to about 100 kDa. In one aspect, the weight average molecular weight is from about 5 kDa to about 60 kDa. In one aspect, the weight average molecular weight is from about 5 kDa to about 55 kDa. In one aspect, the weight average molecular weight is from about 5 kDa to about 50 kDa. In one aspect, the weight average molecular weight is from about 5 kDa to about 45 kDa. In one aspect, the weight average molecular weight is from about 5 kDa to about 40 kDa. In still another aspect, the weight average molecular weight is from about 5 kDa to 35 kDa. In one aspect, the weight average molecular weight is from about 10 kDa to about 60 kDa. In one aspect, the weight average molecular weight is from about 10 kDa to about 55 kDa. In one aspect, the weight average molecular weight is from about 10 kDa to about 50 kDa. In one aspect, the weight average molecular weight is from about 10 kDa to about 45 kDa. In one aspect, the weight average molecular weight is from about 10 kDa to about 40 kDa. In still another aspect, the weight average molecular weight is from about 5 kDa to 35 kDa. In one aspect, the weight average molecular weight is from about 15 kDa to about 60 kDa. In one aspect, the weight average molecular weight is from about 15 kDa to about 55 kDa. In one aspect, the weight average molecular weight is from about 15 kDa to about 50 kDa. In one aspect, the weight average molecular weight is from about 15 kDa to about 45 kDa. In one aspect, the weight average molecular weight is from about 15 kDa to about 40 kDa. In still another aspect, the weight average molecular weight is from about 15 kDa to 35 kDa.

In some embodiments of the product/composition, the biodegradable polymer may make up about 10 wt %, about 15 wt %, about 20 wt %, about 25 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 50 wt %, about 55 wt %, or about 60 wt % of the final composition. In some embodiments, the biodegradable polymer may make up about 20 wt % to about 45 wt % of the final composition. Alternatively, the biodegradable polymer may make up any whole-number weight percentage of the final composition from about 10 wt % to about 60 wt %. In other embodiments, the biodegradable polymer may make up any tenth of a whole number percent of the final composition from about 10 wt % to about 60 wt %. In some embodiments, the polymer in the final pharmaceutical composition as delivered to a subject is present in amounts ranging from about 70 mg to about 175 mg, or from about 75 mg to about 170 mg, or from about 80 to 85 mg, or from about 155 to about 160 mg, or from about 205 to about 215 mg, or from about 160 to about 170 mg. The amount of polymer present in the final pharmaceutical composition can include any whole number from about 70 mg to about 175 mg.

In embodiments, the biodegradable polymers may optionally be purified prior to use in the long-acting formulation to remove low-molecular weight oligomers and/or unreacted monomers, and/or catalyst. Several methods of purifying polymers are known in the art, including the methods described in U.S. Pat. Nos. 4,810,775, 7,019,106, and 9,187,593, among others. In some embodiments of the composition, the biocompatible polymer comprises less than about 0.5%, or less than about 0.4%, or less than about 0.3%, or less than about 0.2% or less than about 0.1% unreacted monomers. In some embodiments of the composition, the biocompatible polymer comprises less than about 0.5%, or less than about 0.4%, or less than about 0.3%, or less than about 0.2% or less than about 0.1% unreacted lactide monomer.

Obtaining a suitable viscosity of the polymer solution may be useful to aid in mixing contents of the first and second containers, which will generally depend on the identity of the polymer (e.g., a PLG polymer at a specific molecular weight and composition), solvent, and concentration of the polymer in solution. This concentration may vary depending on the formulation of the counterpart drug solution. The polymer solution (e.g., the PLG polymer solution) can have a viscosity of 3,000 cP to 50,000 cP, e.g., 3,000 cP to 46,000 cP, 5,000 cP to 46,000 cP, 10,000 cP to 46,000 cP, 15,000 to 46,000 cP, 3,000 cP to 40,000 cP, 5,000 cP to 40,000 cP, 10,000 cP to 40,000 cP, 15,000 to 40,000 cP, 3,000 cP to 35,000 cP, 5,000 cP to 35,000 cP, 10,000 cP to 35,000 cP, 15,000 to 35,000 cP, 3,000 cP to 30,000 cP, 5,000 cP to 30,000 cP, 10,000 cP to 30,000 cP, 15,000 to 30,000 cP, 3,000 cP to 25,000 cP, 5,000 cP to 25,000 cP, 10,000 cP to 25,000 cP, 15,000 to 25,000 cP, 3,000 cP to 20,000 cP, 5,000 cP to 20,000 cP, 10,000 cP to 20,000 cP, or 15,000 to 20,000 cP. Viscosities of the polymer solution such as the PLG solution can be measured at 25° C. using a rotational viscometer (e.g., a cone and plate rheometer, such as a commercially available Brookfield viscometer).

Biocompatible Solvents

Any suitable water-miscible solvent can be employed, provided the solvent is biocompatible, and miscible to dispersible in aqueous medium or body fluid. Examples of suitable solvents are disclosed, e.g., in Aldrich Handbook of Fine Chemicals and Laboratory Equipment, Milwaukee, Wis. (2000); and in U.S. Pat. Nos. 5,324,519; 4,938,763; 5,702,716; 5,744,153; and 5,990,194. In various aspects, the solvent diffuses into body fluid so that the flowable polymer-based composition coagulates, gels or solidifies. The solvent dissolves the polymer. Solvents and co-solvents that may be used in the disclosed compositions are preferably biocompatible, non-toxic, solvents, which may be either hydrophilic or hydrophobic solvents, or may be a combination of hydrophilic solvents, hydrophobic solvents or hydrophilic and hydrophobic solvents, depending upon the desired release profile and the solubility of the polymer and/or the LA API in the polymer/solvent composition. In one aspect, the solvent and/or co-solvent is an organic solvent. In still another aspect, the solvent and/or co-solvents is a polar aprotic solvent.

Suitable solvents and co-solvents may comprise one or more solvents selected from the group consisting of amides, acids, alcohols, esters of monobasic acids, ether alcohols, sulfoxides, lactones, polyhydroxy alcohols, esters of polyhydroxy alcohols, ketones, and ethers. By way of non-limiting example, the solvents or cosolvents may comprise at least one of N-methyl-2-pyrrolidone (NMP), dimethyl sulfoxide (DMSO), 2-pyrrolidone, N,N-dimethylformamide, propylene carbonate (PC), caprolactam, triacetin, dimethylacetamide (DMA), benzyl benzoate (BnBzO), methyl ethyl ketone, methyl lactate, benzyl alcohol, tributyl citrate, acetyl tributyl citrate, acetyl triethyl citrate, triethyl citrate, diethylene glycol monomethyl ether, ethyl acetate, N-ethyl-2-pyrrolidone, glycofurol, polyethylene glycol, or combinations thereof. In one aspect, the biocompatible solvent is DMSO, NMP, ethyl acetate, DMA, BnBzO, benzyl alcohol, or combinations thereof. In one aspect, the biocompatible solvent is DMSO, NMP or a combination thereof. In one aspect, the biocompatible solvent is NMP.

Also disclosed herein, the biodegradable polymer is dissolved in the biocompatible solvent. Further, the LA may be dissolved in a first biocompatible solvent and the biodegradable polymer may be dissolved in a second biocompatible solvent. In one aspect, the first and second biocompatible solvents are the same. In one aspect, the first and second biocompatible solvent is NMP.

The biocompatible solvent, or combination or mixture of solvents and/or co-solvents used in a composition of the disclosure, will generally comprise between about 20 wt % and about 80 wt % of the final formulation, or between about 30 wt % and about 70 wt % of the final formulation, or between about 45 wt % and about 65 wt % of the final formulation, or alternatively the solvent or combination or mixture of solvents and/or co-solvents can range from any whole number percentage by weight of the formulation to any other whole number percentage by weight of the final formulation between about 20 wt % and about 80 wt %.

Additives

Optionally, the pharmaceutical compositions disclosed herein may comprise various additives to improve the stability, the injectability, or/and other properties of the composition. For example, the pharmaceutical products/compositions may comprise one or more of antioxidants, chelating agents, surfactants, co-solvents, stabilizers, complexing agents, excipients, and solubilizers. Importantly, if the pharmaceutical product includes an additive in the second container, i.e., with the LA and solvent, the drug solution concentrations described herein for the LA with respect to the biocompatible solvent is not changed. The amount of additive in the drug-solvent second container must be accounted for and the amount of biocompatible solvent and LA modified accordingly, since the present inventors have discovered that additives seem to act as "competing solutes" rather than "co-solvents" and are likely to disrupt the threshold that was discovered for stable products described herein.

In some embodiments, the pharmaceutical products/compositions may comprise one or more solubilizers to increase the solubility of one or more other component of the composition. Solubilizers useful in the disclosed compositions include any solubilizer useful for parenteral injection, and include, but are not limited to, surfactants which lower the surface tension between two liquids, between a gas and a liquid, or between a liquid and a solid and other solubilizers. Examples of suitable solubilizers and/or surfactants for use in the disclosure include, but are not limited to, polysorbate 20, polysorbate 80, poloxamer 188, sorbitan trioleate, lecithin (e.g., soya or egg), polyethylene glycol (PEG), PEG 300, 2-pyrrolidone, α-tocopherol, Vitamin E TPGS, sugar based esters or ethers (e.g., sugar acid esters of fatty alcohols or sugar alcohol esters of fatty acids, including, but not limited to, sucrose cocoate, sucrose stearate, sucrose laurate, etc.), amino acid-based solubility enhancers (e.g., proline, arginine, DL-methionine), protein-based solubility enhancers (e.g., hydrophobins), and others.

In some embodiments, the pharmaceutical products/compositions may comprise one or more antioxidants to inhibit oxidation of the API and improve the stability of the formulation. Examples of suitable antioxidants for use in the disclosure include, but are not limited to, citric acid, methanesulfonic acid, ascorbic acid, ethylenediaminotetraacetic acid (EDTA), mercaptoethanol, sodium metabisulfite butylated hydroxyanisole, butylated hydroxyquinone, butylhydroxyanisol, hydroxycoumarin, butylated hydroxytoluene, cephalm, ethyl gallate, propyl gallate, octyl gallate, lauryl gallate, propyl-hydroxybenzoate, trihydroxybutylrophenone, dimethylphenol, dibutylphenol, vitamin E, lecithin and ethanolamine.

In some embodiments, the pharmaceutical products/compositions may comprise one or more complexing agents to inhibit oxidation and/or degradation of the API and improve the stability of the formulation. Examples of suitable complexing agents for use in the disclosure include, but are not limited to, ethylenediaminotetraacetic acid (EDTA), divalent metal salts ($ZnCl_2$, $MgCl_2$, $CaCl_2$), nitrilotriacetic acid, n-hydroxyethylethylenediaminetriacetic acid (HEDTA), ethylene glycol-bis(β-aminoethyl ether)-N,N,N',N'-tetraacetic acid (EGTA) as well as several simple organic acids, such as, polycarboxylic acid (citric acid), hydrochloric acid, sulfuric acid, pamoic acid, and palmitic acid.

In some embodiments, the pharmaceutical products/compositions may comprise one or more stabilizing agents to prevent drug and/or polymer degradation and improve the stability of the formulation and increase shelf life. Examples include, but are not limited to: polycarboxylic acids (e.g., citric acid), strong acids (e.g., methanesulfonic acid, sulfuric acid, hydrochloric acid), and hydrophobic acids (e.g., pamoic acid, palmitic acid).

Products/Compositions

In various aspects, the present disclosure provides extended-release, injectable pharmaceutical compositions comprising LA, a biocompatible and biodegradable polymer, a biocompatible solvent, and optionally one or more additives. All such compositions are contemplated for administration to a subject to treat a disease or condition as disclosed herein. In various aspects, the products/compositions of the disclosure are contemplated for use to treat prostate cancer, including advanced prostate cancer; or to treat central precocious puberty (CPP). Further, such products/compositions are contemplated for administration to a subject to reduce luteinizing hormone (LH) levels in a subject in need of LHRH reduction, to reduce serum testosterone levels, and to suppress ovarian function in a subject with HR+ breast cancer palliatively treat cancer in a male with HR+ breast cancer. Further contemplated the pharmaceutical products disclosed herein, can include an amount effective to: (1) treat other diseases or conditions (e.g., including as a palliative therapy) including, but not limited to, hormone-related endometrial cancer, hormone-related ovarian cancer, hormone-related cervical cancer, endometriosis, and fibroids; (2) reducing the levels in a subject of various hormones by GnRH pathways (testosterone, estrogen/estradiol, follicle stimulating hormone (FSH), etc.), (3) suppressing functions associated with hormones in the GnRH pathways, such as suppressing ovarian function in a subject with HR+ breast cancer; and (4) blocking or suppression of hormones in the GnRH pathway for other purposes, such as to prevent or delay puberty in a transgender individual.

The drug solution comprising the LA is dissolved in the biocompatible solvent (as in a solution), and then combined/mixed with the biodegradable polymer dissolved also in solvent (as in a solution).

As provided for herein, the delivered amount in the first and/or second container is the amount (or the contribution) that is delivered to the subject after homogeneous mixing of the contents of the first and second containers occurs.

In some embodiments, the present disclosure provides a pharmaceutical product wherein the biodegradable polymer is a PLG copolymer having at least one hydroxyl end group, wherein the molar ratio of the lactide to glycolide monomers in the copolymer is about 50:50, about 75:25, or about 85:15, and the biocompatible solvent in the first container and the second container is NMP.

In some embodiments, the present disclosure provides a pharmaceutical product wherein the first container delivers about 75 mg to about 90 mg acid-initiated 50:50 PLG copolymer and from about 115 mg to about 170 mg of NMP (e.g., 125 mg to 155 mg); the second container delivers about 6.7 mg to about 8.3 mg LA (e.g., about 7.5 mg LA) and from about 5 mg to about 40 mg NMP; and wherein when contents of the first and second containers are mixed, the resulting composition is an extended-release composition for subcutaneous injection into a subject that upon injection into the subject, forms an in situ depot that releases the LA over a time period of about 1 month. In one aspect, the second container delivers about 7.5 mg LA and about 14.0 mg NMP. In another aspect, the first container delivers about 82.5 mg acid-initiated 50:50 PLG copolymer and about 146 mg NMP. In one aspect, the first and second containers deliver the amounts of LA, NMP, and polymer as shown for any of the illustrative formulations in Table 11.

In some embodiments, the present disclosure provides a pharmaceutical product wherein the first container delivers about 150 mg to about 170 mg of 1,6-hexane-diol initiated 75:25 PLG copolymer (e.g., 155 mg to 165 mg) and from about 90 mg to about 170 mg of NMP; the second container delivers about 20 to about 25 mg LA (e.g., about 22.5 mg) and from about 35 mg to about 105 mg NMP; and wherein when contents of the first and second containers are mixed, the resulting composition is an extended-release composition for subcutaneous injection into a subject that upon injection into the subject, forms an in situ depot that releases the LA over a time period of about 3 months. In one aspect, the second container delivers about 22.5 mg LA and about 42 mg NMP. In still another aspect, the first container delivers about 158.6 mg 1,6-hexane-diol initiated PLG copolymer and about 152 mg NMP. In one aspect, the second container delivers the amounts of LA and NMP and the first container delivers the amounts of polymer and NMP as shown for any of the illustrative formulations in Table 12.

In some embodiments, the present disclosure provides a pharmaceutical product wherein the first container delivers about 185 mg to about 235 mg of 1,6-hexane-diol initiated 75:25 PLG copolymer and from about 120 mg to about 225 mg of NMP; the second container delivers about 27 mg to about 33 mg LA (e.g., about 30 mg) and from about 35 mg to about 135 mg NMP; and wherein when contents of the first and second containers are mixed, the resulting composition is an extended-release composition for subcutaneous injection into a subject that upon injection into the subject, forms an in situ depot that releases the LA over a time period of about 4 months. In one aspect, the second container delivers about 30.0 mg LA and about 57.0 mg NMP. In yet another aspect, the first container delivers about 211.5 mg 1,6-hexane-diol initiated PLG copolymer and about 201.5 mg NMP. In one aspect, the second container delivers the amounts of LA and NMP and the first container delivers the amounts of polymer and NMP as shown for any of the illustrative formulations in Table 13.

In some embodiments, the present disclosure provides a pharmaceutical product wherein the first container delivers about 145 mg to about 185 mg of 1,6-hexane-diol initiated 85:15 PLG copolymer and from about 100 mg to about 170 mg of NMP; the second container delivers 40 mg to about 50 mg LA (e.g., about 45 mg) and from about 55 mg to about 95 mg NMP; and wherein when contents of the first and second containers are mixed, the resulting composition is an extended-release composition for subcutaneous injection into a subject that upon injection into the subject, forms an in situ depot that releases the LA over a time period of about 6 months. In one aspect, the second container delivers about 45.0 mg LA and about 69.6 mg NMP. In still another aspect, the first container delivers about 165 mg 1,6-hexane-diol initiated PLG copolymer and about 153.6 mg NMP. In one aspect, the second container delivers the amounts of LA and NMP and the first container delivers the amounts of polymer and NMP as shown for any of the illustrative formulations in Table 15.

In some embodiments, the present disclosure provides a pharmaceutical product wherein the first container delivers about 145 mg to about 185 mg of 1,6-hexane-diol initiated 75:25 PLG copolymer and from about 80 mg to about 178 mg of NMP; the second container delivers about 27 mg to about 33 mg LA and from about 50 mg to about 135 mg NMP; and wherein when contents of the first and second containers are mixed, the resulting composition is an extended-release composition for subcutaneous injection into a subject that upon injection into the subject, forms an in situ depot that releases the LA over a time period of about 4 months. In one aspect, the second container delivers about 30.0 mg LA and about 57 mg NMP. In still another aspect, the first container delivers about 166 mg 1,6-hexane-diol initiated PLG copolymer and about 157 mg NMP. In one aspect, the second container delivers the amounts of LA and NMP and the first container delivers the amounts of polymer and NMP as shown for any of the illustrative formulations in Table 14.

Additional exemplary embodiments include the following products suitable for administration to subject once per every one month, three months, four months, or six months:

i) A pharmaceutical product suitable for administration to a subject once per every one month, where the biodegradable polymer is a PLG polymer (e.g., a 50:50 PLG or PLGH polymer), the biocompatible solvent is NMP; the first container is formulated to deliver 120 mg to 160 mg NMP (e.g., 125 mg to 155 mg) and 75 mg to 90 mg of the PLG polymer, and the second container is formulated to deliver 7.5 mg leuprolide acetate and 5 mg to 40 mg NMP.

ii) A pharmaceutical product suitable for administration to a subject once per every three months, where the biodegradable polymer is a PLG polymer (e.g., a 75:25 PLG polymer), the biocompatible solvent is NMP; the first container is formulated to deliver 90 mg to 170 mg NMP and 150 mg to 170 mg of the PLG polymer (e.g., 155 mg to 165 mg, or 155 to 160 mg), and the second container is formulated to deliver 22.5 mg leuprolide acetate and 35 mg to 105 mg NMP.

iii) A pharmaceutical product suitable for administration to a subject once per every three months, where the biodegradable polymer is a PLG polymer (e.g., a 75:25 PLG polymer), the biocompatible solvent is NMP; the first container is formulated to deliver 80 mg to 178 mg NMP and 145 mg to 185 mg of the PLG polymer, and the second container is formulated to deliver 30 mg leuprolide acetate and 35 mg to 135 mg NMP.

iv) A pharmaceutical product suitable for administration to a subject once per every four months, where the biodegradable polymer is a PLG polymer (e.g., a 75:25 PLG polymer), the biocompatible solvent is NMP; the first container is formulated to deliver 120 mg to 225 mg NMP and 185 mg to 235 mg of the PLG polymer, and the second container is formulated to deliver 30 mg leuprolide acetate and 35 mg to 135 mg NMP.

v) A pharmaceutical product suitable for administration to a subject once per every six months, where the biodegradable polymer is a PLG polymer (e.g., an 85:15 PLG polymer), the biocompatible solvent is NMP; the first container is formulated to deliver 100 mg to 170 mg NMP and 145 mg to 185 mg of the PLG polymer, and the second container is formulated to deliver 45 mg leuprolide acetate and 50 mg to 95 mg NMP.

In some embodiments, the present disclosure provides an injectable extended release composition which when injected into a subject delivers about 0.433 mL total volume of the composition having about 45.0 mg LA; about 165.0 mg 85:15 PLG copolymer having at least one hydroxyl end group, and about 220 mg NMP, wherein the composition is formulated for subcutaneous administration about once per six months.

In some embodiments, unreacted lactide, caprolactone, and/or glycolide monomers in the polymers or copolymers within the pharmaceutical product and/or the final composition are less than about 1.0 wt %, less than about 0.5 wt %, than about 0.4 wt %, less than about 0.3 wt %, less than about 0.2 wt % and less than about 0.1 wt %.

In various aspects the first and/or second container may be a syringe as disclosed herein. In various aspects the first and second containers are each a chamber of a dual-chambered, single syringe. In one embodiment, the first and second containers are a first and second syringe, respectively. In one embodiment, the first and second syringes are pre-filled with the polymer-solvent solution (first syringe) and the LA-solvent solution (second syringe) and are further provided pre-connected in a kit or package.

Treatment Methods, Uses and Administration

The methods of this disclosure are used in the treatment of diseases or conditions including prostate cancer, including advanced prostate cancer.

Still further, the methods of this disclosure are used in reducing serum testosterone levels in a subject to a level below 20 ng/dL, below 10 ng/dL or lower. In one aspect, the compositions disclosed herein reduce leutenizing hormone (LH) in a subject in need of LHRH, which in one aspect, is reduced to a level less than about 4 IU/L.

In another aspect the reduction of LH levels treats prostate cancer. In yet another aspect, the reduction of LH levels suppresses ovarian function in a subject with hormone receptor positive (HR+) breast cancer in a subject.

Further, the methods of this disclosure are used in suppressing ovarian function in a subject with hormone-receptor positive (HR+) breast cancer. In one aspect, the hormone receptor positive breast cancer is pre-menopausal breast cancer. In one aspect, the hormone receptor positive breast cancer is peri-menopausal breast cancer. In one aspect, the hormone receptor positive breast cancer is estrogen receptor (ER) positive breast cancer. In one aspect, the compositions disclosed herein suppress a subject's estradiol (E2) production to a level less than about 20 pg/mL, less than about 15 pg/mL, less than about 10 pg/mL, less than about 5 pg/mL, less than about 4 pg/ml, less than about 3 pg/mL, or less than about 2 pg/mL. In one aspect, the E2 production level is reduced to about 2.7 pg/mL. In still another aspect, the compositions disclosed herein suppresses the breast cancer subject's follicle stimulating hormone (FSH) to a level less than about 40 IU/L. In yet another aspect, the compositions disclosed herein suppresses the breast cancer subject's leutenizing hormone (LH) to a level less than about 4 IU/L.

Still further, the methods of this disclosure are used in treating endometriosis or uterine fibroids, or other hormone-related cancers including hormone-related endothelial cancer or hormone-related ovarian cancer.

The methods of this disclosure are used in the treatment of central precocious puberty (CPP). CPP is defined by early sexual development prompted by production and release of gonadotropins and/or sex steroids from normal endogenous sources including the hypothalamus or pituitary. Aberrations in gonadotropin and/or sex hormone concentration levels in children with CPP can result from various sources, including, but not limited to, physical injury, infection, genetic disease, or associated tumors. CPP caused by a genetic or undetermined pathology is classified to be idiopathic in nature, while CPP caused by a central nervous system (CNS) tumor and/or lesion is classified as organic in nature. CPP is accompanied by advanced bone age, accelerated growth velocity, and Hypothalamic-Pituitary-Gonadal-axis activation. In one aspect, the compositions disclosed herein reduce a subject having CPP blood serum LH concentration to a pre-pubertal concentration levels of <4 IU/L.

The methods and/or uses disclosed herein comprise subcutaneously administering to the subject's disclosed herein, the disclosed extended-release injectable compositions subsequent to mixing the contents of the first container comprising the biodegradable polymer disclosed herein dissolved in a biocompatible solvent disclosed herein, and the second container comprising the drug solution (DS) comprising LA dissolved in the biocompatible solvent disclosed herein, wherein the DS concentration is no more than 45% w/w LA in the biocompatible solvent. Upon injection of the extended-release pharmaceutical composition into the body and contact of the composition with a bodily fluid, the solvent dissipates, forming a drug reservoir or depot. The resulting depot will release the LA, over a desired extended time period. In various embodiments, the LA is released into a subject/patient, for a period of at least about 30 days or longer, at least about 60 days or longer, at least about 90 days or longer, at least about 120 days or longer, at least about 150 days or longer, or 180 days or longer. In still other embodiments, the LA is released into a subject/patient, for a period of at least about one month or longer, at least about two months or longer, at least about three months or longer, at least about four months or longer, at least about five months or longer, or six months or longer. In still other embodiments, the LA is released into a subject/patient for a period of at least about four weeks or longer, at least about eight weeks or longer, at least about twelve weeks or longer, at least about sixteen weeks or longer, at least about 20 weeks or longer, or at least about 24 weeks or longer.

The extended-release composition may be administered to the patient/subject about every 30 days (e.g., once every 30 days), about every 60 days, about every 90 days, about every 120 days, about every 150 days or about every 180 days. In another aspect, the extended-release composition may be administered to the patient/subject about every 1 month (e.g., about once every month), about every 2 months, about every 3 months, about every 4 months, about every 5 months or about every 6 months. In another aspect, the extended-release composition may be administered to the patient/subject about every four weeks, about every eight weeks, about every twelve weeks, about every sixteen weeks, about every 20 weeks, or about every 24 weeks.

Preferably, the disclosed extended-release compositions are to be administered to a subject/patient once in a dosing period with varying durations, or a non-variable duration, between dosing periods (e.g., one month, 2 months, 3 months, 4 months, 5 months, or 6 months). In one aspect, there may be a single loading dose or alternatively two or three loading doses, followed by maintenance doses having a defined interval between doses. The loading dose(s) may provide a different amount of LA API to the patient, or the same amount of LA API to the patient, as compared to the maintenance dose. Dosing may be provided alone or in combination with other drugs and may continue as long as required for effective treatment of the disease state or disorder.

In some embodiments, the composition is terminally sterilized by irradiation (such as e-beam, Gamma irradiation, or X-ray). In yet another aspect, the composition is sterile filtered.

In some embodiments, the extended-release composition(s) disclosed herein is administered as a monotherapy to patients. The therapeutic methods of this embodiment may reduce or eliminate one or more symptoms of the disease and/or condition disclosed herein. In other embodiments, the long-acting composition may be administered as a combination therapy, such as with chemotherapeutics, radiation therapy, surgery, endocrine therapies such as selective estrogen receptor modulators (SERMs; such as tamoxifen, toremifene, raloxifene, ospemifene, and bazedoxifene), selective estrogen receptor degraders (SERDs; such as fulvestrant), aromatase inhibitors (AIs; such as anastrozole, letrozole, exemestane, vorozole, formestane, and fadrozole); mammalian target of rapamycin (mTOR) inhibitors; such as temsirolimus, sirolimus, everolimus, and ridaforolimus); Phosphatidylinositol 3-kinases inhibitors (PI-3 kinase or PI3K; such as alpelisib, idelalisib, and buparlisib); cyclin-dependent kinases 4 and 6 inhibitors (CDK4/6 inhibitors; such as abemaciclib, palbociclib, and ribociclib); other LURH agonists (such as other salts of leuprolide, gonadorelin, goserelin, histrelin, nafarelin, buserelin, and triptorelin and their pharmaceutically acceptable salts thereof), immuno-therapy, and gene therapy.

The disclosed products/compositions may be provided as a part of a delivery system comprising a syringe system, wherein the product/composition is contained within syringes. Accordingly, such delivery systems are within the scope of the present disclosure.

For the pre-filled syringe delivery system for administration of the product/composition disclosed herein, the first container is a first syringe comprising the polymer-solvent solution and the second container is a second syringe comprising the drug-solvent solution. In one aspect of this system, the first syringe and the second syringe are coupled together to mix the contents of the first and second syringe. In the prefilled syringe system disclosed herein, the polymer solution of the first syringe is mixed with the drug solution of the second syringe to form an extended-release composition for subcutaneous injection into a subject. A plurality of mixing cycles is performed to mix the contents of the first syringe with the contents of the second syringe to visual and/or substantial homogeneity. As used herein, homogeneity can mean a visually uniform depot for injection or wherein the homogeneity is substantially similar at the beginning, middle, and end of syringe mixing as measured via an in-unit content uniformity assay, or wherein homogeneity of a between-unit delivered dose content uniformity is substantially similar. In one aspect, the contents of the first syringe and the second syringe require at 30 cycles of mixing or fewer, 25 cycles of mixing or fewer, 20 cycles of mixing or fewer, 15 cycles of mixing or fewer, 10 cycles of mixing or fewer, or 5 cycles of mixing or fewer. In one aspect, the contents of the first syringe and second syringe require 5-30 cycles of mixing, 10-30 cycles of mixing, 20-30 cycles of mixing, 5-20 cycles of mixing, 10-20 cycles of mixing, or 5-10 cycles of mixing.

The composition may be administered by manual injection or automated though a syringe with, for example, a 16 to 24 gauge needle, or an 18 to 22 gauge needle, or an 18 to 20 gauge needle with standard, or thin wall, or extra thin walls.

Also contemplated herein is a kit comprising a prefilled syringe system disclosed herein and instructions for mixing and administration.

EXAMPLES

The following examples describe methods used to prepare and test the extended-release compositions disclosed herein.

Preparation of Polymers

Polymers were either purchased (commercially available poly(D,L-lactide-co-glycolide) polymers sold under the trademark RESOMER®) or synthesized in-house. Poly(D,L-lactide-co-glycolide) (PLG) copolymers, poly-DL-lactide (PLA) polymers, or poly(D,L-lactide-co-caprolactone) (PDLCL or PLC) copolymers were produced using the following methods. The amounts of monomers (DL-lactide or glycolide or caprolactone) and initiator (e.g., glycolic acid, 1,6-Hexanediol, polyethylene glycol (PEG)) were selected to obtain a targeted initiator, monomer molar ratio, and weight average molecular weight for each investigated polymer. The monomer molar ratios and weight average molecular weights reported in individual examples are targeted values unless specified as actual or experimental. The polymerization was conducted in a stirred, heated vessel under a nitrogen atmosphere. In the vessel, appropriate amounts of monomers (DL-lactide and/or glycolide and/or caprolactone, and initiator (glycolic acid or 1,6-Hexanediol) were added, the vessel contents were placed under a nitrogen atmosphere. The temperature of the vessel was increased until the reagents melted. A catalyst solution was made with appropriate amounts of stannous octoate and toluene and added to the vessel. The vessel was then heated to about 140-170° C. under a nitrogen atmosphere for about 4-18 hours (depending on the polymer of interest) with constant stirring. Then, the vessel was evacuated to remove unreacted monomers, and the monomers were vacuum-distilled out of the polymerization mixture. The hot melt was then extruded into cooling pans. After cooling, the solid mass was broken up into smaller pieces. The polymer was purified as needed using the solvent/non-solvent-induced phase separation method.

Preparation of Bulk Polymer Solutions and Prefilled Syringes (First Container-Syringe A) of Polymer Solution Polymer bulk solutions were prepared by weighing a known amount of each polymer material into individual Flack-Tek jars of the desired size. A known amount of NMP was added to each polymer, and the containers were placed on a horizontal jar mill or Turbula for mixing at room temperature. Jars were mixed until a visually clear homogenous polymer solution is obtained indicating the complete dissolution of the polymer in the solvent. Prefilled syringes (First container—Syringe A) containing polymer delivery system were prepared by weighing the required amounts of polymer solution into 1.2 mL female polypropylene syringe barrel with Luer lock and plunger tip and capped with male polypropylene syringe cap, 1.2 mL male cyclic olefin copolymer syringes, or 1 mL male cyclic olefin copolymer syringes with female polypropylene cap. Filled syringes were then packaged in labeled foil pouches with a Syringe B and a desiccant pack and the pouches were sealed. After filling the syringes with the formulations, they were terminally sterilized with an external radiation dose of 30 kGy e-beam processing. Terminally sterilized syringes kits were stored under refrigerated conditions (e.g., 2-8° C.) or accelerated conditions (≥25° C. see individual experiments) in the sealed foil pouches.

Preparation of LA-DS Organic-Solvent Bulk Solution and Prefilled Syringes (Second Container-Syringe B)

To produce the drug/solvent bulk solution comprising the API (LA), the desired amount of the LA was combined with the solvent NMP or DMSO or combination of solvents with or without a co-solvent or other additives, in the indicated amounts (see individual experiments below). The API and solvent were combined in a glass vial or jar. Jars were mixed using the jar mill, Turbula, or shaker at room temperature until homogeneous. LA is soluble in NMP or DMSO and can load higher concentrations (at least 40% w/w). After dissolving the API in the organic solvent, the bulk solution was manually filled into syringes and capped with a tip cap. The syringes used for filling were either 1.2 mL male polypropylene syringes, 1.2 mL male cyclic olefin copolymer syringes or 1 mL male cyclic olefin copolymer syringes. Filled syringes were then packaged in labeled foil pouches with a Syringe A (polymer-solvent solution) and a desiccant pack and the pouches were sealed. After filling the syringes with the formulations, they were terminally sterilized with an external radiation dose of 30 kGy from e-beam processing. After terminal sterilization, the syringes were stored under refrigerated conditions (e.g., 2-8° C.) or accelerated conditions (≥25° C. see individual experiments).

Preparation of Final Formulation for Administration:

Immediately before administering, "A" and "B" syringes were allowed to equilibrate to room temperature for not less than 30 minutes. The syringes were coupled and mixed by cycling the contents from one syringe to the other to visual and/or substantial homogeneity. The mixed formulation was fully transferred to the male dosing syringe for delivery and testing. A safety needle of 18 or 20 g was used for delivering the formulation when needed during testing.

Analysis of LA-DS in the Formulations

LA/organic solvent solutions were prepared for HPLC analysis by dilution to volume with mobile phase A (0.1% trifluoroacetic acid water) and mixing thoroughly by vortex. Dilutions were performed as needed using volumetric glassware and mixed thoroughly by vortex mixing. A second dilution of 2 mL to 20 mL was performed with mobile phase A to obtain a working sample.

For the HPLC test sample preparation of formulations that contain polymer, syringe A and syringe B were coupled together and mixed for 45 cycles. The product was dispensed from the final mixed syringe formulation content into a 50 mL volumetric flask and the weight was recorded. 2.0 mL of mobile phase B (0.1% trifluoroacetic acid acetonitrile) was added and mixed by swirling. 3.0 mL of mobile phase A was added and mixed by swirling. Samples were placed in a water bath at 55° C.±2° C. for 30 minutes and then cooled to room temperature. Samples were diluted to volume with mobile phase A and mixed thoroughly by vortex, followed by dilution to 20 mL with mobile phase A with thorough mixing. A second dilution of 2 mL to 20 mL was performed with mobile phase A to obtain a working sample. The sample solutions were filtered through a 0.45 um PTFE syringe filter into amber HPLC vials before collection into the HPLC vial.

Additionally, samples of the liquid-liquid drug product were prepared by mixing for the indicated number of cycles and dispensed into an organic solution comprising acetonitrile, methanol, and trifluoroacetic acid. The drug product was dissolved via vortex as before and then diluted to 100 mL with a predominantly aqueous diluent of water, acetonitrile, and trifluoroacetic acid. Filtration and subsequent dilutions of the stock to an approximate concentration of 30 to 40 µg/mL of leuprolide were performed to generate working samples.

HPLC analysis for assay and related compounds was performed using an Agilent AdvanceBio Peptide 3.0×100 mm, 2.7 um column and an Agilent AdvanceBio Peptide Map Guard 3.0×5 mm 2.7 um guard column at 30° C. with a flow rate of 0.75 mL/min. The runtime was 15 minutes with a 10-µL injection for assay and related compounds for the solution gel depot formulation, and a 20-µL injection for assay and related compounds for the polymer depot formulation. Detection was performed with a diode array detector set at 220 nm.

Additionally, HPLC analysis was also performed using a Waters Cortecs UPLC column and matching guard column at 40° C. with a 0.5 mL/min flow rate. A gradient method utilizing both acidic water and acetonitrile was employed to sufficiently separate N-methyl pyrrolidone and leuprolide. Detection was performed with a diode array detector set to 220 nm.

In-Vitro Release Testing and F2 Similarity Calculations

Dissolution media was prepared for In-Vitro release analysis of formulations. A precise volume of media was measured into a glass jar and conditioned to 60° C. in a temperature-controlled reciprocating water bath prior to formulation reconstitution. Room temperature samples were mixed per package instructions and transferred into Syringe B for addition to release media. An 18- or 20-gauge needle was attached to Syringe B for controlled expression of the homogeneous formulation into a 60° *C. media* jar using a syringe pump. Jars were removed from the reciprocating bath and 2 mL of media was sampled just below the surface of the media at pre-determined time points for each formulation. These media samples were then analyzed for LA content by HPLC similar to the above HPLC assay description. The in-vitro release data is summarized in FIG. 4, FIG. 5, FIG. 6, and FIG. 7. F2 similarity calculations were performed to compare liquid-liquid with liquid-solid formulation in vitro performance for each dosage strength. These similarity calculations showed there are no statistically significant differences between liquid-liquid and liquid-solid formulations.

Animal Dosing

First container comprising the polymer-solvent solutions (Syringe A) and the second container comprising the LA solvent solutions (Syringe B) were prepared as described above. For animal study dose administration, the LA content was measured by HPLC assay. This % w/w LA in the homogeneous formulation was used to calculate dosing volume for animal subjects at a predetermined amount of LA per kilogram of body weight. The calculated volume for each formulation was transferred to a graduated 100 microliter Hamilton syringe and injected through an 18- or 20-gauge needle into the subjects. LA absorption rates were obtained using a rat model. Male rats were each injected with a single subcutaneous injection of the extended-release compositions/formulations. The composition of the formulations are listed in Tables 1-5. At predetermined time points, rats were bled and plasma LA levels were determined using liquid chromatography with tandem mass spectrometry (LC-MS/MS). Each data point is based on an average plasma or average serum LA concentration. Six rats were dosed for each group, with sparse blood sampling performed for early time points. A drug product that is a liquid-solid formulation (containing the same polymer-solvent but in the amounts indicated in Syringe A and lyophilized LA in Syringe B as indicated in the table) was included in each study as a control.

TABLE 1

Comparison of Contents in Syringe A/B for Liquid-Solid Formulations vs Container A/B for Liquid-Liquid Formulations - 7.5 mg

| | | Liquid-Solid Formulation | | Liquid-Liquid Formulation | |
|---|---|---|---|---|---|
| Component | Excipient | % w/w | Delivered Mass (mg) | % w/w | Delivered Mass (mg) |
| Delivery System (Syringe A) | 50:50 Poly(DL-lactide-co-glycolide) | 33.0 | 82.5 | 33.0 | 82.5 |
| | N-methyl-2-pyrrolidone | 64.0 | 160.0 | 58.4 | 146.0 |
| Drug Substance (Syringe B) | Leuprolide Acetate | 3.0 | 7.5 | 3.0 | 7.5 |
| | N-methyl-2-pyrrolidone | N/A | N/A | 5.6 | 14.0 |
| Final Delivered Product | | 250 mg | | 252 mg | |

TABLE 2

Comparison of Contents in Syringe A/B for Liquid-Solid Formulations vs Container A/B for Liquid-Liquid Formulations - 22.5 mg

| | | Liquid-Solid | | Liquid-Liquid | |
|---|---|---|---|---|---|
| Component | Excipient | % w/w | Delivered Mass (mg) | % w/w | Delivered Mass (mg) |
| Delivery System (Syringe A) | 75:25 Poly(DL-lactide-co-glycolide) | 42.3 | 158.6 | 42.3 | 158.6 |
| | N-methyl-2-pyrrolidone | 51.7 | 193.9 | 40.3 | 151.1 |
| Drug Substance (Syringe B) | Leuprolide Acetate | 6.0 | 22.5 | 6.0 | 22.5 |
| | N-methyl-2-pyrrolidone | N/A | N/A | 11.4 | 42.8 |
| Final Delivered Product | | 375 mg | | 375 mg | |

TABLE 3

Comparison of Contents in Syringe A/B for Liquid-Solid Formulations vs Container A/B for Liquid-Liquid Formulations - 30 mg

| | | Liquid-Solid | | Liquid-Liquid | |
|---|---|---|---|---|---|
| Component | Excipient | % w/w | Delivered Mass (mg) | % w/w | Delivered Mass (mg) |
| Delivery System (Syringe A) | 75:25 Poly(DL-lactide-co-glycolide) | 42.3 | 211.5 | 42.3 | 211.5 |
| | N-methyl-2-pyrrolidone | 51.7 | 258.5 | 40.3 | 201.5 |

TABLE 3-continued

Comparison of Contents in Syringe A/B for Liquid-Solid Formulations vs Container A/B for Liquid-Liquid Formulations - 30 mg

| | | Liquid-Solid | | Liquid-Liquid | |
|---|---|---|---|---|---|
| Component | Excipient | % w/w | Delivered Mass (mg) | % w/w | Delivered Mass (mg) |
| Drug Substance (Syringe B) | Leuprolide Acetate | 6.0 | 30.0 | 6.0 | 30.0 |
| | N-methyl-2-pyrrolidone | N/A | N/A | 11.4 | 57.0 |
| Final Delivered Product | | 500 mg | | 500 mg | |

TABLE 4

Comparison of Contents in Syringe A/B for Liquid-Solid Formulations vs Container A/B for Liquid-Liquid Formulations - 45 mg

| | | Liquid-Solid | | Liquid-Liquid | |
|---|---|---|---|---|---|
| Component | Excipient | % w/w | Delivered Mass (mg) | % w/w | Delivered Mass (mg) |
| Delivery System (Syringe A) | 85:15 Poly(DL-lactide-co-glycolide) | 44.0 | 165.0 | 38.1 | 165.0 |
| | N-methyl-2-pyrrolidone | 44.0 | 165.0 | 35.5 | 153.6[1] |
| Drug Substance (Syringe B) | Leuprolide Acetate | 12.0 | 45.0 | 10.4 | 45.0 |
| | N-methyl-2-pyrrolidone | N/A | N/A | 16.0 | 69.6[1] |
| Final Delivered Product | | 375.0 mg | | 433.2 mg | |

[1]Total NMP delivered from the Liquid-Liquid product is 223.2 mg, 58.2 mg higher than the NMP in the Liquid-Solid 45 mg formulation. This corresponds to a 35.3% difference in delivered NMP and a 15.5% difference in final product delivered mass.

TABLE 5

Comparison of Contents in Syringe A/B for Liquid-Solid Formulations vs Container A/B for Liquid-Liquid Formulations - 30 mg

| | | Liquid-Solid | | Liquid-Liquid | |
|---|---|---|---|---|---|
| Component | Excipient | % w/w | Delivered Mass (mg) | % w/w | Delivered Mass (mg) |
| Delivery System (Syringe A) | 75:25 Poly(DL-lactide-co-glycolide) | 41.7 | 166 | 40.4 | 165.6 |
| | N-methyl-2-pyrrolidone | 50.8 | 202 | 38.4 | 157.4 [1] |
| Drug Substance (Syringe B) | Leuprolide Acetate | 7.5 | 30 | 7.3 | 30 |
| | N-methyl-2-pyrrolidone | N/A | N/A | 13.9 | 57.0 [1] |
| Final Delivered Product | | 398 mg | | 410 mg | |

[1] Total NMP delivered from the Liquid-Liquid product is 213 mg, 11 mg higher than the Liquid-Solid formulation. This corresponds to a 5.32% difference in delivered NMP and a 2.76% difference in final product delivered mass.

Figure 2:
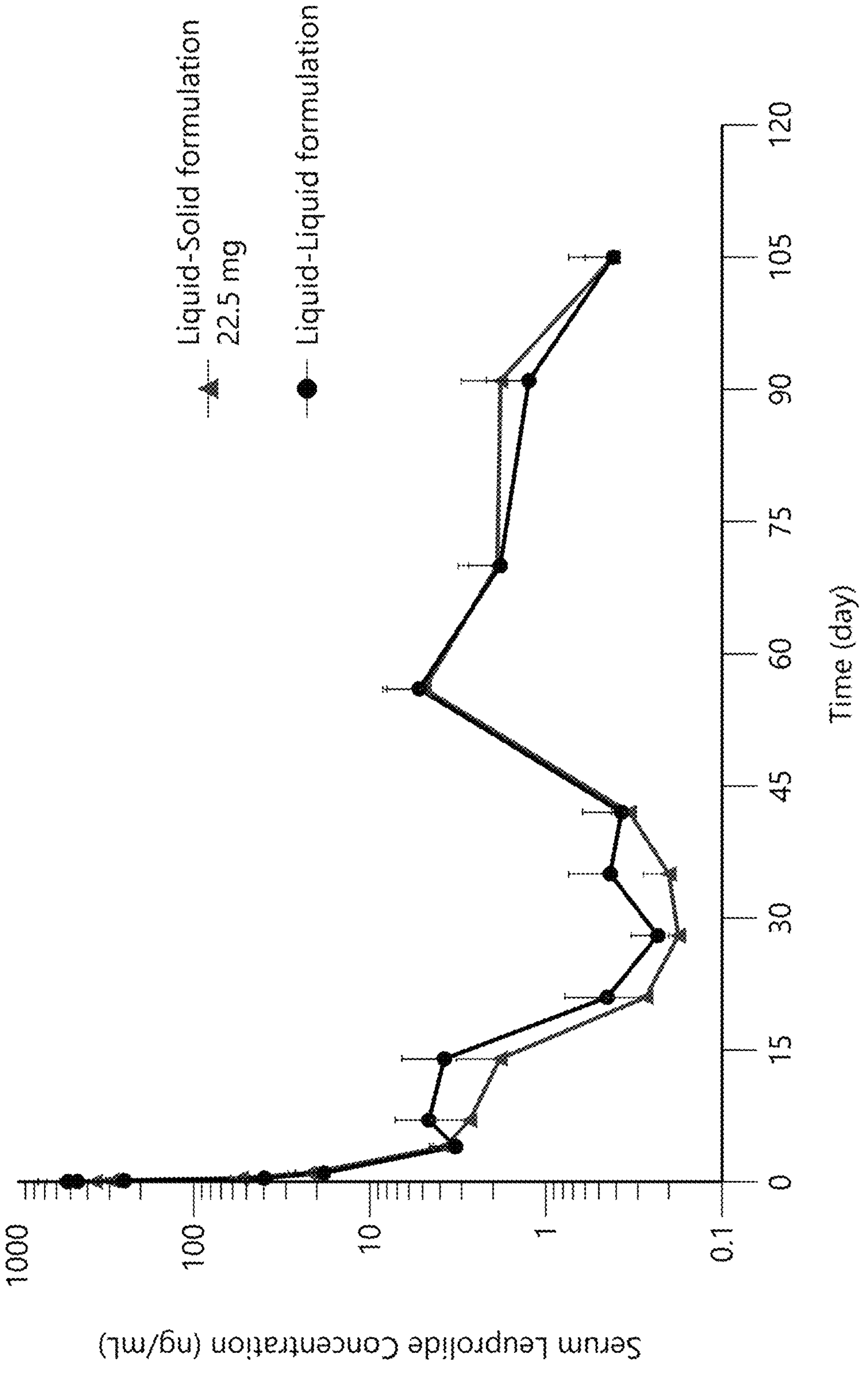
FIG. 2 shows PK study blood serum LA concentration results comparing liquid-solid to liquid-liquid 22.5 mg formulations.
Figure 3:
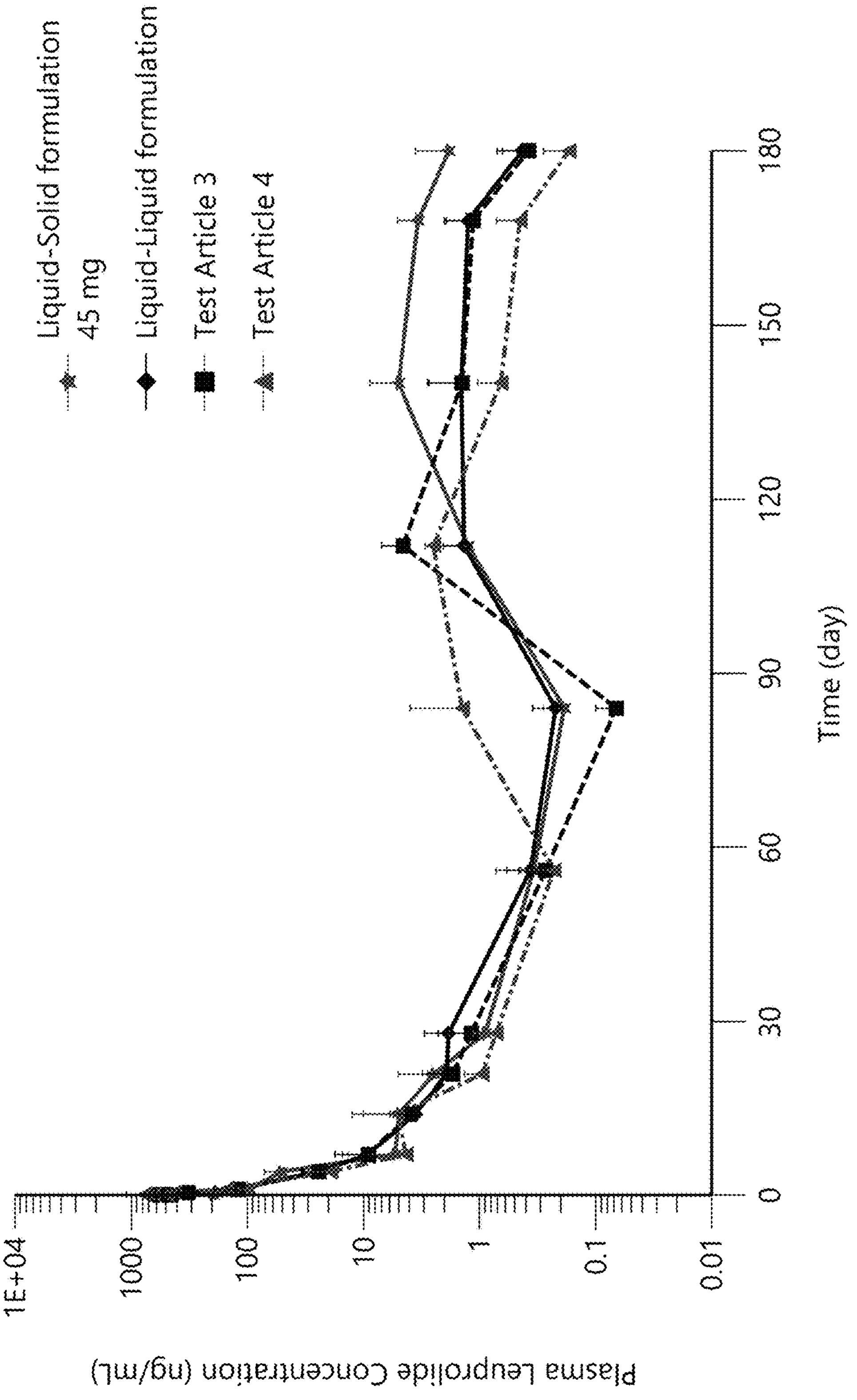
FIG. 3 shows PK study blood plasma LA concentration results comparing liquid-solid formulation to liquid-liquid 45 mg formulation and liquid-liquid formulations with additional solvent; Test Article 3 (244 mg NMP) and Test Article 4 (259 mg NMP).
Figure 4:
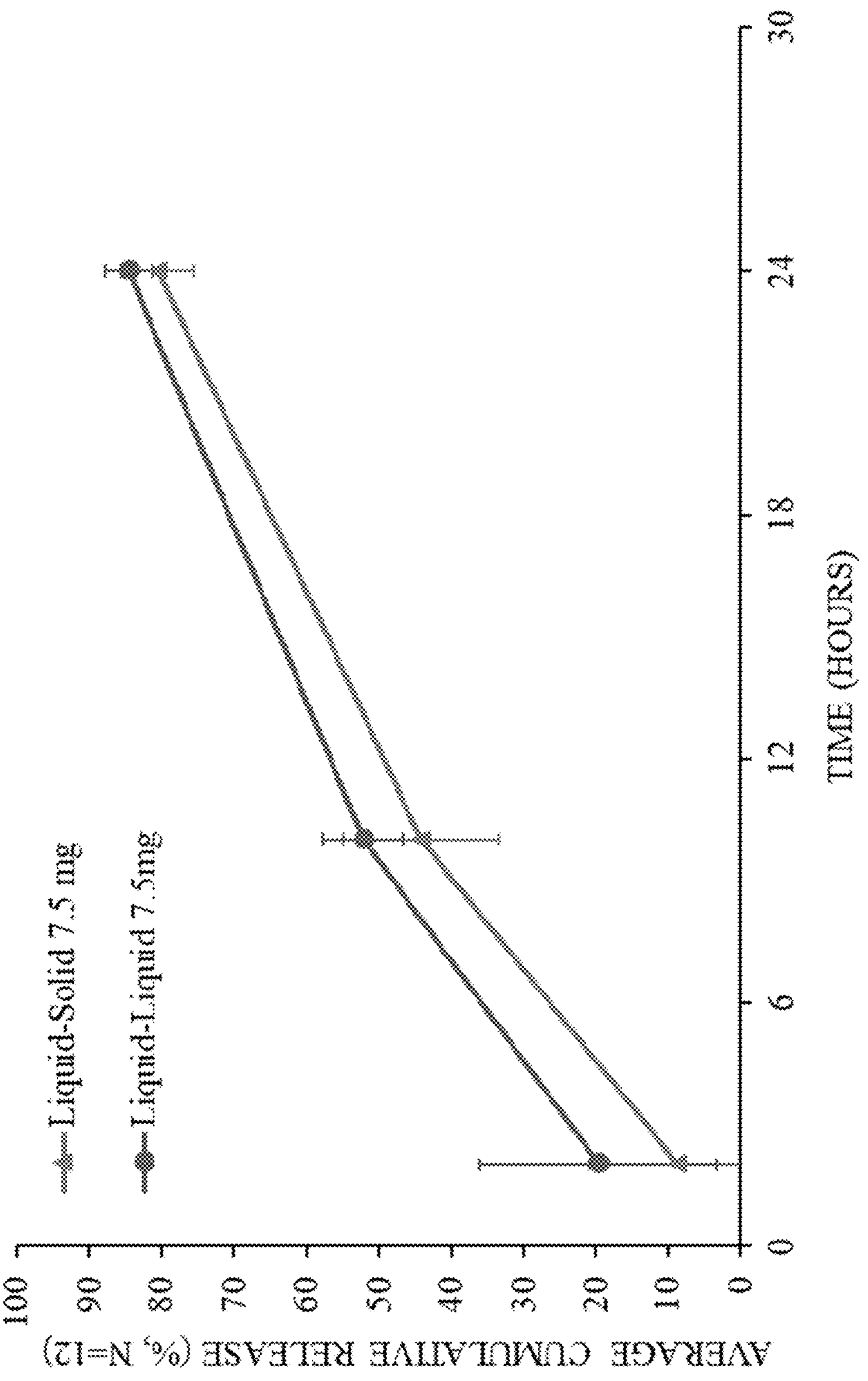
FIG. 4 shows in vitro data comparing the average cumulative percent release of LA from the polymer depot for liquid-solid and liquid-liquid 7.5 mg formulations.
Figure 5:
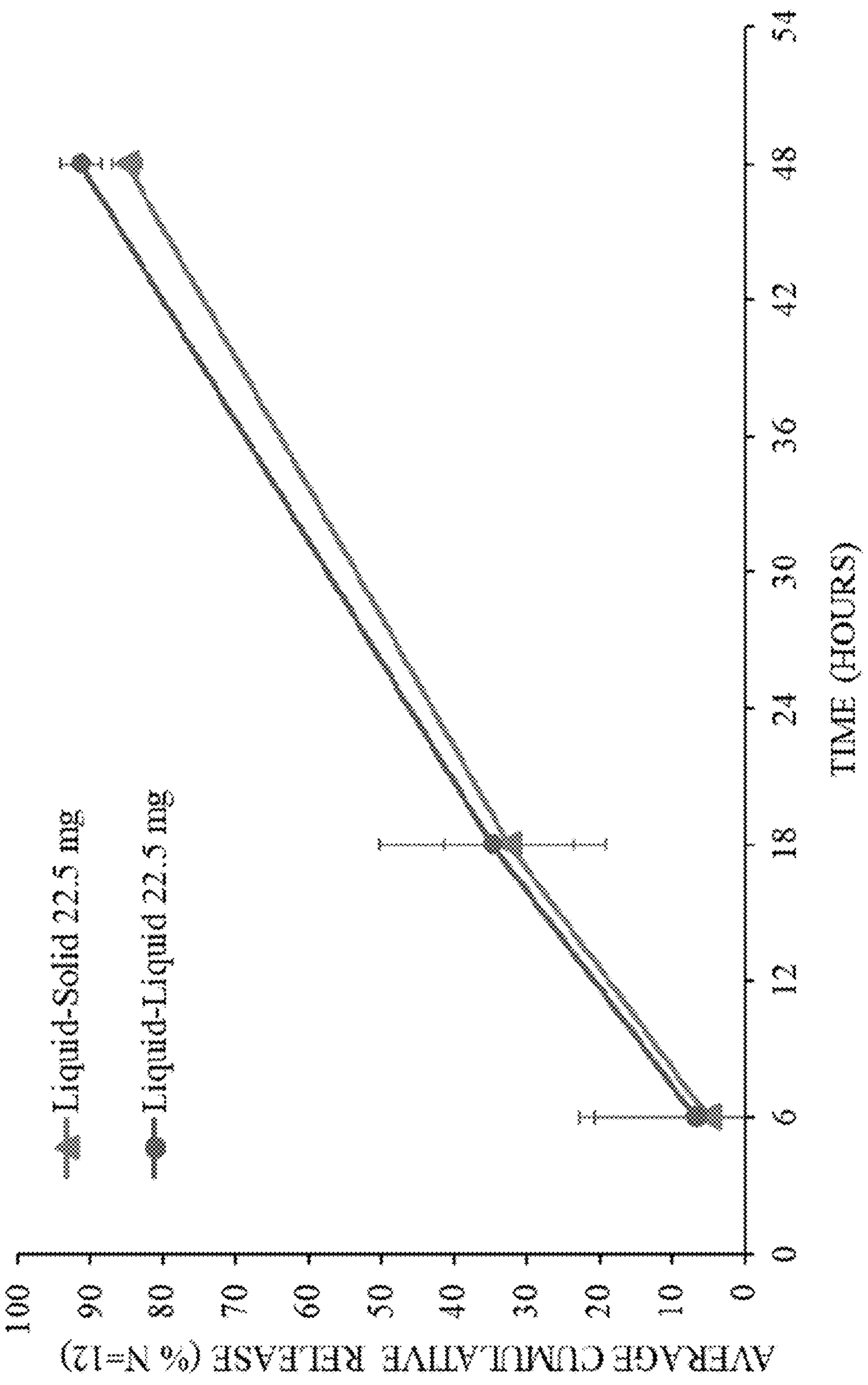
FIG. 5 shows in vitro data comparing the average cumulative percent release of LA from the polymer depot for liquid-solid and liquid-liquid 22.5 mg formulations.
Figure 6:
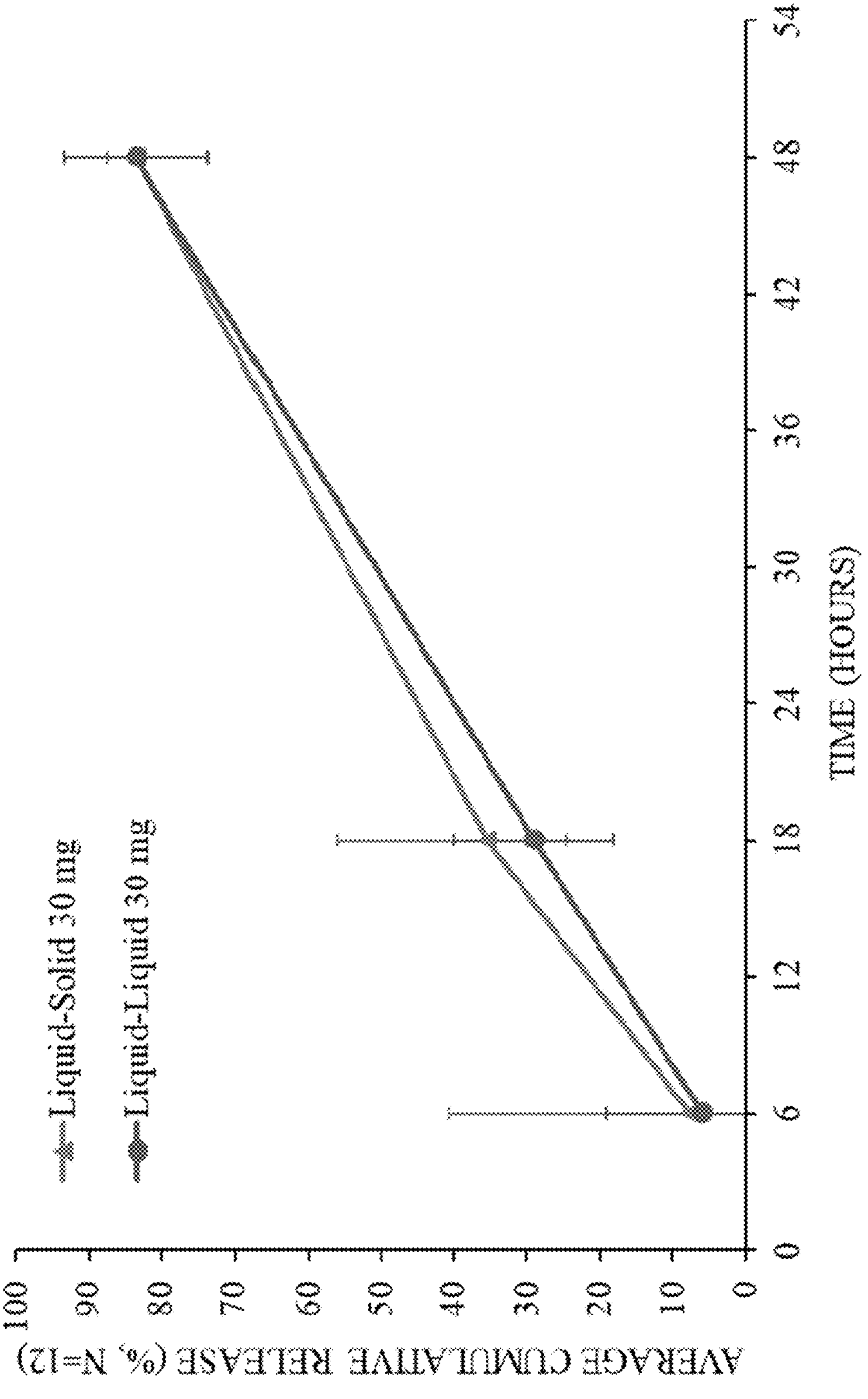
FIG. 6 shows in vitro data comparing the average cumulative percent release of LA from the polymer depot for liquid-solid and liquid-liquid 30 mg formulations.
Figure 7:
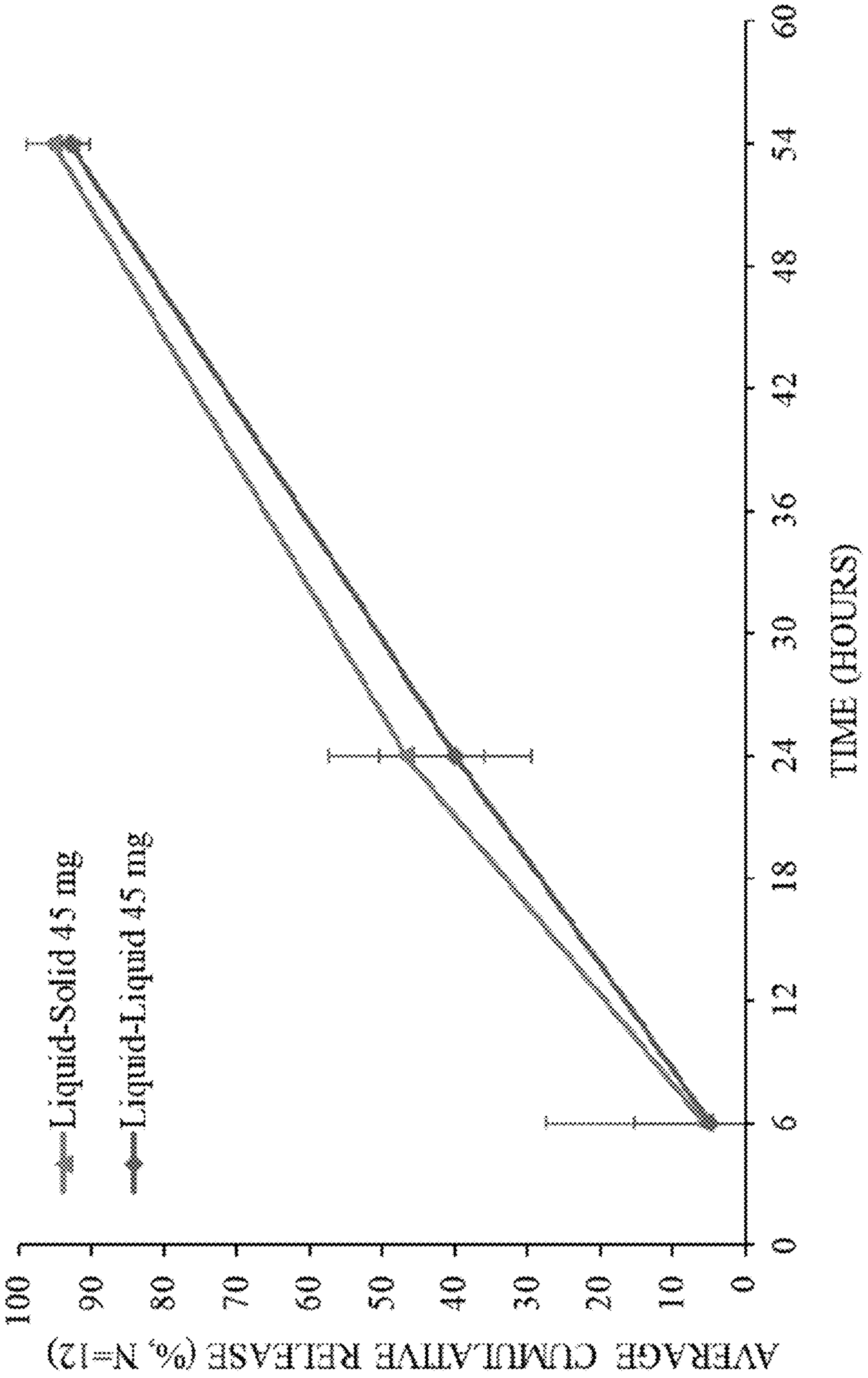
FIG. 7 shows in vitro data comparing the average cumulative percent release of LA from the polymer depot for liquid-solid and liquid-liquid 45 mg formulations.

Blood plasma or some instances serum concentrations of LA are presented for each study in FIG. 1A, FIG. 2, and FIG. 3. $C_{max}$ and $AUC_{last}$ were similar for the Liquid-Liquid formulations when compared to the corresponding Liquid-Solid formulations delivering 7.5 mg, 22.5 mg, and 45 mg as controls.

7.5 mg Product:

The LA plasma concentration data of the Liquid-Liquid 7.5 mg product demonstrates similar controlled release exposure of this combination product to the liquid-solid 7.5 mg control (FIG. 1A). This is specifically observed in the results after day 28; where LA release is complete (day 35 and 45 concentrations were below the limit of quantification (BLQ)). No significant difference was observed for Liquid-Solid 7.5 mg formulation and the Liquid-Liquid 7.5 mg formulation mean±standard error of the mean (SEM) $AUC_{last,\ 0\text{-}28d}$ (106.09±7.94 and 91.66±11.56, respectively; p-value 0.3209, n=8). In addition, no significant difference was observed for Liquid-Solid 7.5 mg formulation and the Liquid-Liquid 7.5 mg formulation mean $C_{max}$±SEM (384.25=20.22 and 410±31.56, respectively; p-value 0.5033, n=8). Similarly, the Liquid-Liquid 20% LA formulation was comparable to both the Liquid-Solid and Liquid-Liquid 7.5 mg formulations.

TABLE 6

PK Parameters for 7.5 mg and 20% LA Formulations

| Group | Liquid-Solid formulation 7.5 mg | Liquid-Liquid formulation | Liquid-Liquid 20% LA Drug Substance Formulation |
|---|---|---|---|
| Cmax (ng/mL) (mean +/− SE) | 384.25 ± 20.22 | 410.00 ± 31.56 | 460.00 ± 30.08 |
| P value | — | 0.5033 | 0.0581 |
| AUC0-28 d (day*ng/mL) (mean +/− SE) | 106.09 ± 7.94 | 91.66 ± 11.56 | 81.72 ± 4.28 |
| P value | — | 0.3209 | 0.02097 |

22.5 mg Product:

As shown in FIG. 2, no significant difference was observed for Liquid-Solid 22.5 mg formulation and the Liquid-Liquid 22.5 mg product mean±SEM $AUC_{last,\ 0\text{-}105d}$ (335.74±35.25 and 332.23±35.25, respectively; p-value 0.9368, n=6). In addition, no significant difference was observed for Liquid-Solid 22.5 mg formulation and the Liquid-Liquid 22.5 mg formulation mean $C_{max}$±SEM (544.33±79.51 and 519±139.20, respectively; p-value 0.8776, n=6). Serum LA concentrations were BLQ after study day 105.

45 mg Product:

In addition to the Liquid-Liquid 45 mg product, the impact of increased final delivered product NMP content on PK was investigated. Table 6 details the composition of each test formulation delivering the same amount of LA and polymer as Liquid-Solid 45 mg formulation while varying the amount of delivered NMP. The range of NMP content studied was designed to span from delivered amounts of Liquid-Solid 45 mg formulation (165 mg NMP) to Liquid-Solid 30 mg formulation (258.5 mg NMP) in the 45 mg Liquid-Liquid formulations. The results through day 180 show similar PK profiles for the control and all test articles.

TABLE 7

45 mg Formulations Studied in the Animal Model

| Product | Liquid-Solid Formulation | Liquid-Liquid Formulation Device | | |
|---|---|---|---|---|
| Excipient | Liquid-Solid Control | Liquid-Liquid Formulation | Test Article 3 | Test Article 4 |
| Delivery System (Syringe A/Tip Chamber) | 50% PLG 50% NMP | 55% PLG 45% NMP | 52.5% PLG 47.5% NMP | 50% PLG 50% NMP |
| Drug Substance (Syringe B/Flange Chamber) | 100% LA | 35% LA/65% NMP | | |
| Final Delivered Product NMP % | 44.0% | 51.5% | 52.9% | 54.5% |
| Target Delivered Mass | 375 mg | 445 mg | 460 mg | 475 mg |
| Theoretical Delivered NMP | 165 mg | 229 mg | 244 mg | 259 mg |

TABLE 8

Pharmacokinetic Parameters of LA following a single subcutaneous injection of Liquid-Solid 45 mg and Liquid-Liquid formulations with various NMP concentrations

| Group | Liquid-Solid 45 mg (mean ± SEM, n = 6) | Liquid-Liquid (mean ± SEM, n = 6) | Test Article 3 (mean ± SEM, n = 6) | Test Article 4 (mean ± SEM, n = 6) |
|---|---|---|---|---|
| $C_{max}$ (ng/mL) | 532.33 ± 41.90 | 550.67 ± 39.75 | 572.00 ± 115.05 | 763.33 ± 193.78 |
| p value compared to Liquid-Solid 45 mg | — | 0.7575 | 0.7526 | 0.271 |
| $AUC_{last,\ 0\text{-}180\ d}$ (day*ng/mL) | 885.35 ± 116.75 | 834.57 ± 105.83 | 873.93 ± 42.23 | 918.14 ± 59.72 |
| p value compared to Liquid-Solid 45 mg | — | 0.754 | 0.9296 | 0.8093 |

The non-GLP in vivo studies show that the Liquid-Liquid formulations are similar in release to that of the Liquid-Solid 7.5 mg, 30 mg, and 45 mg formulations. The Liquid-Liquid 45 mg formulation, which contains an additional 58 mg of NMP, does not alter LA exposure. NMP is a biocompatible organic solvent currently used in various marketed products including the leuprolide acetate extended-release injectable suspension sold under the trademark ELIGARD®, the buprenorphine extended-release injection sold under the trademark SUBLOCADE®, and the risperidone extended-release injectable suspension sold under the trademark PERSERIS® up to 833 mg per unit dose. NMP is also listed in the Inactive Ingredient Database for subcutaneous administration at 376 mg per unit dose.

In general, it is established that concentration of drug, polymer, and solvent in in situ forming depots is an important factor in controlling depot formation and associated drug release. See, e.g., Gomaa, E.; Eissa, N. G.; Ibrahim, T. M.; El-Bassossy, H. M.; El-Nahas, H. M.; Ayoub, M. M. "Development of depot PLGA-based in-situ implant of Linagliptin: Sustained release and glycemic control." Saudi Pharm J 2023, 31 (4), 499-509; Parent, M.; Nouvel, C.; Koerber, M.; Sapin, A.; Maincent, P.; Boudier, A. "PLGA in situ implants formed by phase inversion: critical physicochemical parameters to modulate drug release." J Control Release 2013, 172 (1), 292-304. The window in which solvent concentration may be tuned without substantially affecting the release rate depends on the identity of the polymer, the drug, and solvent. Therefore, to minimize the risk of changes in in vivo release profile, it the mixed product composition was maintained as close to the liquid/solid formulation as possible.

LA Gelation Studies

Drug solutions were prepared as described above and filled into syringes or glass vials. Syringes were untreated, contained various amounts of silicone, or were plasma coated for lubrication. Samples were irradiated by e-beam irradiation at not less than 25 kGy and stored at accelerated conditions of 60° C. with agitation at 150 rpm for up to 16 days. Samples were inspected periodically to determine if the drug solution remained a solution or had formed a solid/gel by an inversion test. Samples that had "gelled" were transferred to 5° C. for subsequent testing.

The gelation rate for each sample was calculated as Rate=1/(simulated 5° C. age at time of gelation in days). The Arrhenius equation was used to determine the simulated age, assuming standard reaction rate doubling for every 10° C. increase in temperature. Samples that did not gel were given a gelation rate of 0. Data was analyzed using JMP. Variables related to peptide concentration in the solution (drug solution concentration, leuprolide content, and assay) and their interactions significantly contributed to gelation rate ($p<0.05$). Container type and lubrication were not significant.

Figure 8:
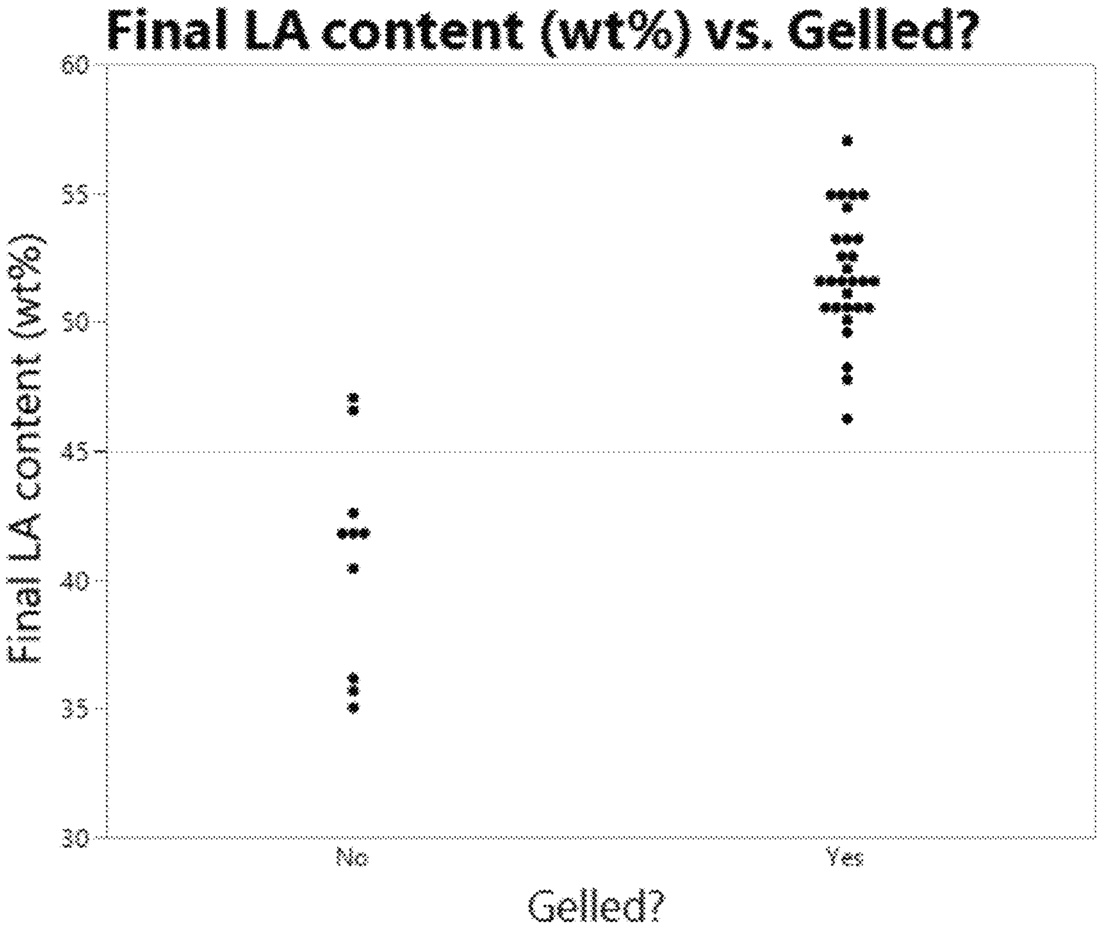
FIG. 8 shows in vitro data from a design of experiments (DOE) study showing the gelation threshold concentration for leuprolide acetate and solvent in a drug solution.

Samples were tested for leuprolide content by HPLC. Leuprolide content was then converted to leuprolide acetate by multiplying by 1.078 (based on molecular mass ratios). The results are shown in FIG. 8. A marked difference in leuprolide acetate content between the gelled and non-gelled samples was seen, with the tipping point between solution and solid/gelled samples occurring at about 45% LA.

Comparative Example Demonstrating Instability of Pre-Mixed System 55.5 wt % polymer solution was prepared by combining 85:15 PLG polymer and NMP in a container and mixing on a Turbula until homogeneous. 39.96 wt % LA drug solution was similarly prepared by combining LA and NMP in a container and mixing on a Turbula until homogeneous. Drug and polymer solutions were then filled into separate syringes, the syringes coupled, and the two solutions were mixed. After mixing, samples were stored at 37° C. Samples were periodically tested for polymer Mw and LA content. The simulated 5° C. age was calculated using the Arrhenius equation assuming the reaction rate doubles for every 10° C. increase in temperature. A decrease in both polymer Mw and LA assay was detected over time, indicating the polymer and drug are not stable long-term when mixed.

TABLE 9

Reduction of Polymer $M_w$ and LA Assay in Pre-Mixed System

| 37° C. Age (weeks) | Approx. 5° C. age (weeks) | Polymer Mw (Da) | PDI | LA Assay (% w/w) |
|---|---|---|---|---|
| 0 | 0 | 22,097 | 1.54 | 10.174 |
| 1 | 9 | 16,822 | 1.55 | 7.418 |
| 2 | 18 | 13,706 | 1.59 | 7.674 |

Examples Demonstrating Importance of Polymer Solution Viscosity

Figure 9A:
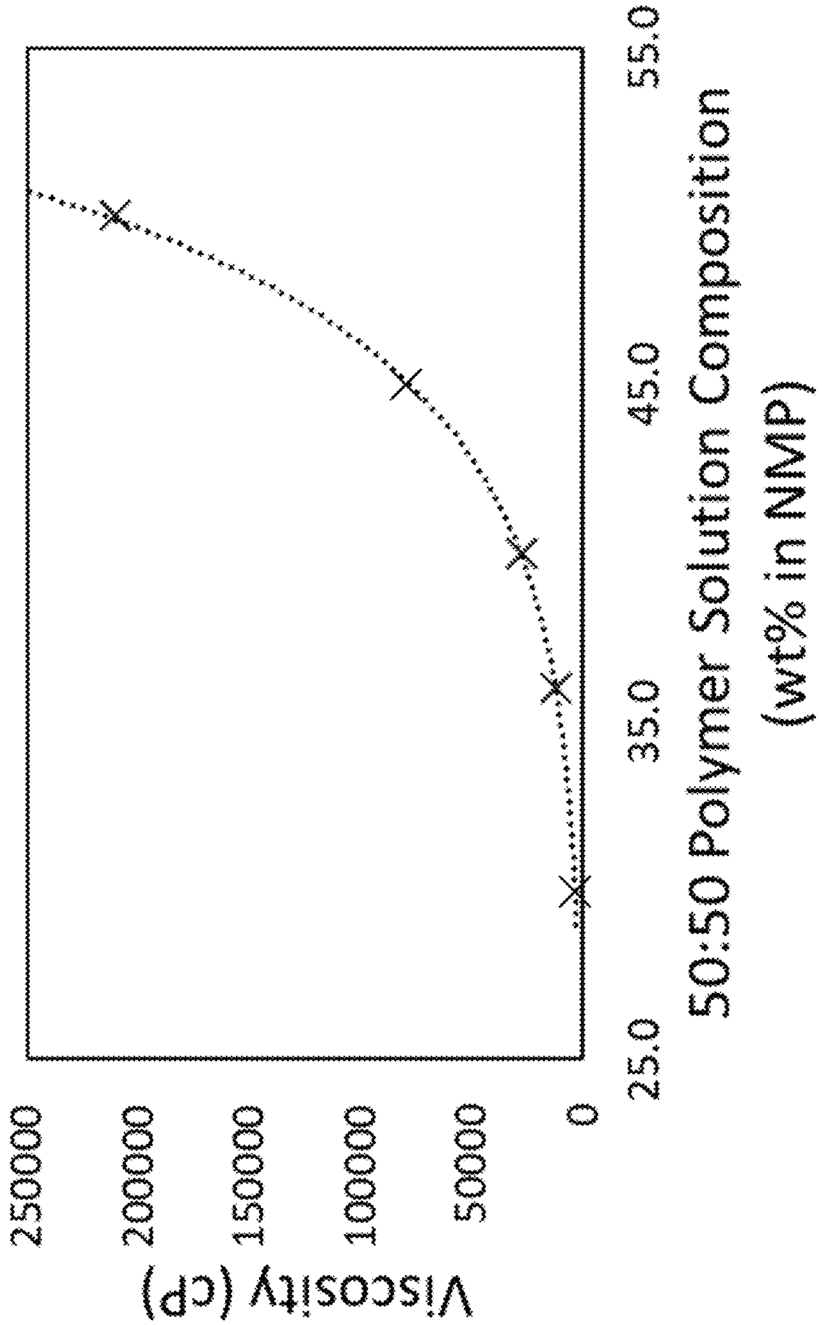
FIG. 9A is a plot of viscosity versus polymer solution composition (wt % in NMP) for a 50:50 PLG polymer.
Figure 9B:
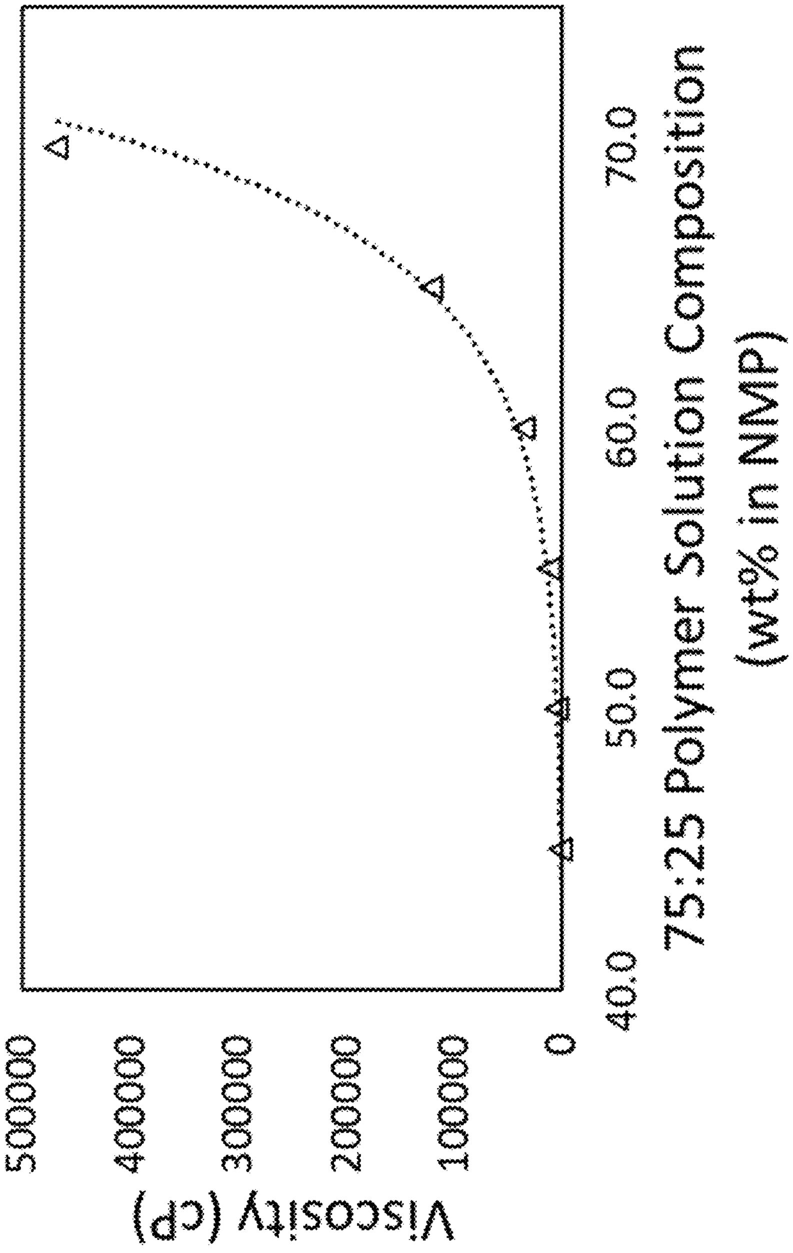
FIG. 9B is a plot of viscosity versus polymer solution composition (wt % in NMP) for a 75:25 PLG polymer.
Figure 9C:
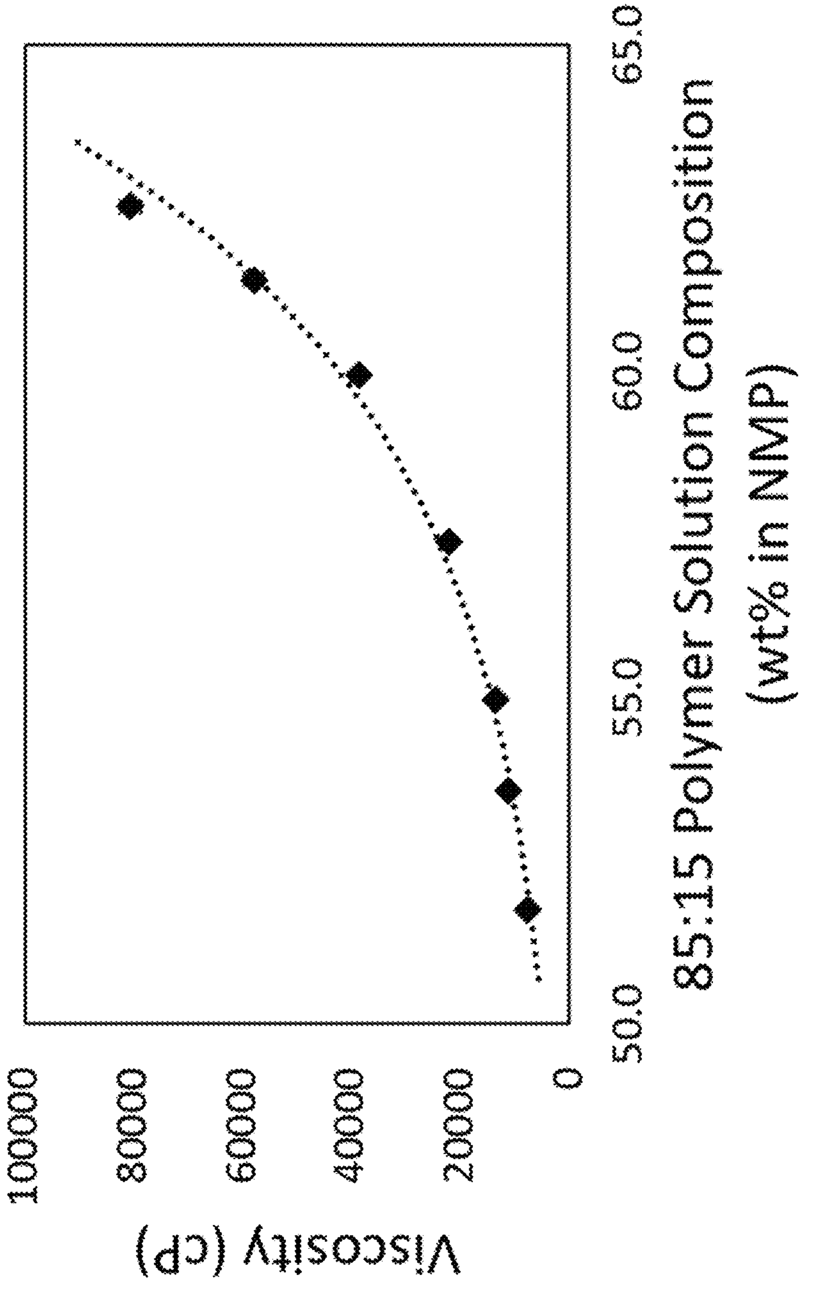
FIG. 9C is a plot of viscosity versus polymer solution composition (wt % in NMP) for a 85:15 PLG polymer.

Polymer solutions were prepared by combining polymer and NMP in a container and mixing on a Turbula, rotisserie, or Flaktek mixer with or without gentle heating until homogeneous. Viscosity testing was performed using a Brookfield R/S CPS+ rheometer at 25° C. with a C50-1 cone or a RCT-50-1 cone. Samples were tested with 2-6 replicates and the average result reported. An exponential curve was fit for each polymer, shown in FIGS. 9A-C.

TABLE 10

Solution Composition Viscosity Relationship for PLG Polymers

| Polymer Solution | | | NMP removed | Corresponding drug solution |
|---|---|---|---|---|
| Polymer ID | Weight % | Viscosity (cP) | from polymer solution (mg) | composition (wt % LA) |
| 50:50 PLG | 30.0 | 3,687 | — | — |
| (7.5 mg | 34 | — | 0 | 100 |
| strength) | 36.0 | 12,702 | 13 | 36 |
| | 40.0 | 28,037 | 36 | 17 |
| | 45.0 | 80,183 | 59 | 11 |
| | 50.0 | 210,995 | 78 | 9 |
| 75:25 PLG | 45.0 | 1,885 | 0 | 100 |
| (22.5 and | 50.0 | 4,597 | 35 | 39 |
| 30 mg | 55.0 | 11,760 | 64 | 26 |
| strengths) | 60.0 | 35,666 | 88 | 20 |
| | 65.0 | 122,297 | 109 | 17 |
| | 70.0 | 469,010 | 126 | 15 |
| 85:15 PLG | 50 | — | 0 | 100 |
| (45 mg | 51.7 | 7,366 | 11 | 81 |
| strengths) | 53.6 | 11,204 | 22 | 67 |
| | 55.0 | 13,374 | 30 | 60 |
| | 57.4 | 21,673 | 43 | 51 |
| | 59.9 | 39,029 | 55 | 45 |
| | 61.4 | 57,879 | 61 | 42 |
| | 62.5 | 80,514 | 66 | 41 |

The results show an exponential relationship, with solutions becoming increasingly viscous as polymer concentration increases. An exponential curve was fit to each dataset. For the 50:50 PLG solutions, Viscosity (cP)= $8.4757*e^{0.2028*polymer\ solution\ \%}$. For the 75:25 PLG solutions, Viscosity (cP)=$0.0771*e^{0.2202*polymer\ solution\ \%}$. For the 85:15 PLG solutions, Viscosity (cP)=$0.0945*e^{0.2169*polymer\ solution\ \%}$. High viscosities, e.g., those above about 20,000 cP, can present challenges for filling syringes with respect to necessary throughput, accuracy, and precision. Additionally, mixing the viscous solution by the user can be difficult due to the high forces required. Therefore, it can be advantageous to remove only a certain amount of NMP from the polymer solution and add this NMP to the drug solution to dissolve the LA. This creates an effective lower limit on the wt % of the drug solution in some embodiments.

For the 7.5 mg formulation (using the 50:50 polymer), keeping polymer solution viscosity below 20,000 cP corresponded to a polymer composition of less than or equal to about 38.3%. Keeping total NMP constant, this relates to a drug composition of 22%. This is below the 45% LA limit where gelation issues were seen (Table 11).

TABLE 11

Illustrative Liquid-Liquid Formulations - 7.5 mg/1 month

| | | | Component | | | | | |
|---|---|---|---|---|---|---|---|---|
| | | | Delivery system (Syringe A) | | | Drug Substance (Syringe B) | | Total |
| | | | 50:50 PLGH | NMP | PS Viscosity (cP)[1] | LA | NMP | (mg) |
| Liquid- Solid Formulation | | % w/w | 34.0 | 66.0 | 8370 | 100 | N/A | 250 |
| | | Delivered Mass (mg) | 82.5 | 160.0 | | 7.5 | | |
| Liquid-Liquid Formulation | 45% LA DS | % w/w | 35.4 | 64.6 | 11,000 | 45 | 55 | 250 |
| | | Delivered Mass (mg) | 82.5 | 151 | | 7.5 | 9 | |
| | 34% LA DS | % w/w | 36.2 | 63.8 | 13,100 | 34 | 66 | 250 |
| | | Delivered Mass (mg) | 82.5 | 145 | | 7.5 | 15 | |
| | 27% LA DS | % w/w | 37.1 | 62.9 | 15,700 | 27 | 73 | 250 |
| | | Delivered Mass (mg) | 82.5 | 140 | | 7.5 | 20 | |
| | 24% LA DS | % w/w | 37.7 | 62.3 | 17,700 | 24 | 76 | 250 |
| | | Delivered Mass (mg) | 82.5 | 136 | | 7.5 | 24 | |
| | 20% LA DS | % w/w | 38.8 | 61.2 | 22,200 | 20 | 80 | 250 |
| | | Delivered Mass (mg) | 82.5 | 130 | | 7.5 | 30 | |

[1]Per prediction equation: Viscosity (cP) = 8.4757 * $e^{0.2028 * \text{polymer solution } \%}$ and rounded to 3 significant figures.

For the 22.5 and 30 mg formulations (using the 75:25 PLG), keeping polymer solution viscosity below 20,000 cP corresponded to a polymer composition of less than or equal to about 56.600. Keeping total NMP constant, this relates to a drug composition of 240%. This is below the 4500 LA limit where gelation issues were seen (Tables 12-14).

TABLE 12

Illustrative Liquid-Liquid Formulations - 22.5 mg/3 month

| | | | Component | | | | | |
|---|---|---|---|---|---|---|---|---|
| | | | Delivery system (Syringe A) | | | Drug Substance (Syringe B) | | Total |
| | | | 75:25 PLG | NMP | PS Viscosity (cP)[1] | LA | NMP | (mg) |
| Liquid- Solid Formulation | | % w/w | 45 | 55 | 1,550 | 100 | N/A | 375 |
| | | Delivered Mass (mg) | 158.6 | 193.9 | | 22.5 | | |
| Liquid-Liquid Formulation | 45% LA DS | % w/W | 48.8 | 51.2 | 3,580 | 45 | 55 | 375 |
| | | Delivered Mass (mg) | 158.6 | 166.4 | | 22.5 | 27.5 | |
| | 34% LA DS | % w/w | 51.4 | 48.6 | 6,350 | 34 | 66 | 375 |
| | | Delivered Mass (mg) | 158.6 | 150.0 | | 22.5 | 43.9 | |
| | 27% LA DS | % w/w | 54.4 | 45.6 | 12,300 | 27 | 73 | 375 |
| | | Delivered Mass (mg) | 158.6 | 132.9 | | 22.5 | 61.0 | |

TABLE 12-continued

Illustrative Liquid-Liquid Formulations - 22.5 mg/3 month

| | | Component | | | | | |
|---|---|---|---|---|---|---|---|
| | | Delivery system (Syringe A) | | | Drug Substance (Syringe B) | | |
| | | 75:25 PLG | NMP | PS Viscosity (cP)[1] | LA | NMP | Total (mg) |
| 24% LA DS | % w/w | 56.4 | 43.6 | 19,100 | 24 | 76 | 375 |
| | Delivered Mass (mg) | 158.6 | 122.6 | | 22.5 | 71.3 | |
| 20% LA DS | % w/w | 60.4 | 39.6 | 46,000 | 20 | 80 | 375 |
| | Delivered Mass (mg) | 158.6 | 104.0 | | 22.5 | 89.9 | |

[1]Per prediction equation: Viscosity (cP) = 0.0771 * $e^{0.2202 * polymer\ solution\ \%}$ and rounded to 3 significant figures.

TABLE 13

Illustrative Liquid-Liquid Formulations - 30 mg/3 month

| | | | Component | | | | | |
|---|---|---|---|---|---|---|---|---|
| | | | Delivery system (Syringe A) | | | Drug Substance (Syringe B) | | |
| | | | 75:25 PLG | NMP | PS Viscosity (cP)[1] | LA | NMP | Total (mg) |
| Liquid- Solid Formulation | | % w/w | 45 | 55 | 1,550 | 100 | N/A | 398 |
| | | Delivered Mass (mg) | 166 | 202 | | 30 | | |
| Liquid-Liquid Formulation | 45% LA DS | % w/w | 50.1 | 49.9 | 4,770 | 45 | 55 | 398 |
| | | Delivered Mass (mg) | 166 | 165.3 | | 30 | 36.7 | |
| | 34% LA DS | % w/w | 53.6 | 46.4 | 10,300 | 34 | 66 | 398 |
| | | Delivered Mass (mg) | 166 | 143.7 | | 30 | 58.3 | |
| | 27% LA DS | % w/w | 57.6 | 42.1 | 26,600 | 27 | 73 | 398 |
| | | Delivered Mass (mg) | 166 | 120.7 | | 30 | 81.1 | |
| | 24% LA DS | % w/w | 60.8 | 39.2 | 50,300 | 24 | 76 | 398 |
| | | Delivered Mass (mg) | 166 | 107.0 | | 30 | 95.0 | |
| | 20% LA DS | % w/w | 66.9 | 33.1 | 193,000 | 20 | 80 | 398 |
| | | Delivered Mass (mg) | 166 | 82.1 | | 30 | 119.9 | |
| | 34% LA DS | % w/w | 51.5 | 48.5 | 6,500 | 34 | 66 | 411 |
| | (+13 mg NMP) | Delivered Mass (mg) | 166 | 156.3 | | 30 | 58.3 | |
| | 20% LA DS | % w/w | 60.4 | 39.6 | 46,000 | 20 | 80 | 425 |
| | (+27 mg NMP) | Delivered Mass (mg) | 166 | 120.0 | | 30 | 120 | |
| | 20% LA DS | % w/w | 56.4 | 43.6 | 19,100 | 20 | 80 | 444 |
| | (+46 mg NMP) | Delivered Mass (mg) | 166 | 128.3 | | 30 | 120 | |

TABLE 14

Illustrative Liquid-Liquid Formulations - 30 mg/4 month

| | | | Component | | | | | |
|---|---|---|---|---|---|---|---|---|
| | | | Delivery system (Syringe A) | | | Drug Substance (Syringe B) | | Total |
| | | | 75:25 PLG | NMP | PS Viscosity (cP)[1] | LA | NMP | (mg) |
| Liquid- Solid Formulation | | % w/w | 45 | 55 | 1,550 | 100 | N/A | 500 |
| | | Delivered Mass (mg) | 211.5 | 258.5 | | 30 | | |
| Liquid-Liquid Formulation | 45% LA DS | % w/w | 48.8 | 51.2 | 3,580 | 45 | 55 | 500 |
| | | Delivered Mass (mg) | 211.5 | 221.9 | | 30 | 36.6 | |
| | 34% LA DS | % w/w | 51.4 | 48.6 | 6,350 | 34 | 66 | 500 |
| | | Delivered Mass (mg) | 211.5 | 200 | | 30 | 58.5 | |
| | 27% LA DS | % w/w | 54.4 | 45.6 | 12,300 | 27 | 73 | 500 |
| | | Delivered Mass (mg) | 211.5 | 177.3 | | 30 | 81.2 | |
| | 24% LA DS | % w/w | 56.4 | 43.6 | 19,100 | 24 | 76 | 500 |
| | | Delivered Mass (mg) | 211.5 | 163.5 | | 30 | 95.0 | |
| | 20% LA DS | % w/w | 60.4 | 39.6 | 46,000 | 20 | 80 | 500 |
| | | Delivered Mass (mg) | 211.5 | 138.7 | | 30 | 119.8 | |

[1]Per prediction equation: Viscosity (cP) = 0.0771 * $e^{0.2202 * \text{polymer solution \%}}$ and rounded to 3 significant figures.

For the 45 mg formulation (using the 85:15 PLG), keeping polymer solution viscosity below 20,000 cP corresponded to a polymer composition of less than or equal to about 56.500. Keeping total NMP constant, this relates to a drug composition of 5400 which is above the limit where gelation occurs. Therefore, it was useful to add additional NMP to the formulation to meet both the polymer and the drug solution composition parameters. To minimize the risk of changes in depot formation and in vivo release behavior, additional NMP was minimized (Table 15).

TABLE 15

Illustrative Liquid-Liquid Formulations - 45 mg/6 months

| | | | Component | | | | | |
|---|---|---|---|---|---|---|---|---|
| | | | Delivery system (Syringe A) | | | Drug Substance (Syringe B) | | Total |
| | | | 85:15 PLG | NMP | PS Viscosity (cP)[1] | LA | NMP | (mg) |
| Liquid- Solid Formulation | | % w/w | 50 | 50 | 4,850 | 100 | NA | 375 |
| | | Delivered Mass (mg) | 165.0 | 165.0 | | 45 | | |
| Liquid-Liquid Formulation | 45% LA DS | % w/w | 60.0 | 40.0 | 42,400 | 45 | 55 | 375 |
| | | Delivered Mass (mg) | 165.0 | 110 | | 45 | 55 | |
| | 45% LA DS (+55 mg NMP) | % w/w | 50 | 50 | 4,850 | 45 | 55 | 430 |
| | | Delivered Mass (mg) | 165.0 | 165.0 | | 45 | 55 | |
| | 34% LA DS (+55 mg NMP) | % w/w | 55.4 | 44.6 | 15,600 | 34 | 66 | 430 |
| | | Delivered Mass (mg) | 165.0 | 132.8 | | 45 | 87.2 | |

[1]Per prediction equation: Viscosity (cP) = 0.0945 * $e^{0.2169 * \text{polymer solution \%}}$ and rounded to 3 significant figures.

Improved Mixing and Stability with Liquid-Liquid Formulations

Polymer solutions were prepared by combining polymer and NMP in a container and mixing on a Turbula, rotisserie, or Flaktek mixer with or without gentle heating until homogeneous. Polymer solutions were filled into male (for liquid-liquid formulations) or female (for liquid-solid formulations) syringes. Liquid-liquid formulation drug syringes were prepared by dissolving LA in NMP, gently mixing on a Turbula, rotisserie, or Flaktek mixer until uniform, and then filled into male syringes. Solid drug syringes were prepared by dissolving LA in water, gently mixing until dissolved. Solution was filled into male syringes, and then lyophilized to remove water.

Syringes were coupled using either a male to female (liquid-solid) or male to male (liquid-liquid) couplers with similar fluid paths. They were then packaged in foil pouches or trays and irradiated by e-beam irradiation at not less than 25 kGy. Syringes were mixed for the indicated number of mixing cycles and delivered via an 18 G (45 mg/6 mo) or 20 G (22.5 mg/3 mo) needle. The mixed product was delivered and tested for LA assay, which was expressed as a 0% of the target weight 0% in the formulation. The average, standard deviation, and RSD (Stdev/Ave*1000) were then calculated.

Fill weight for these formulations were not finalized in these experiments, as seen by the average assay values not being at 10000 of target. However, consistency in the mixed product can be evaluated by comparing the RSD values between groups. Per the package insert for Eligard®, Liquid-Solid formulations should be mixed 60 cycles prior to use. This ensures a well-mixed, consistent product. As can be seen, the liquid-liquid formulations have similar or lower RSDs compared to the liquid-solid formulations with substantially fewer mixing cycles.

TABLE 16

22.5 mg/3 Month Delivered Dose Consistency

| | Liquid - Solid 100% | Liquid-Liquid | | | |
|---|---|---|---|---|---|
| | LA + 45% Polymer | 20.0% LA + 60.4% Polymer | 21.8% LA in Drug Syringe + 58% Polymer | 34.2% LA + 51.4% Polymer | 35.1% LA + 52.0% Polymer |
| Mixing Cycles | 60 | 20 | 20 | 20 | 20 |
| N | 6 | 6 | 6 | 10 | 6 |
| Ave (% target) | 119.6 | 113.0 | 95.4 | 108.3 | 103.9 |
| Stdev (% target) | 5.8 | 4.0 | 3.9 | 2.7 | 5.6 |
| RSD (%) | 4.8 | 3.5 | 4.1 | 2.5 | 5.4 |

TABLE 17

45 mg/6 month Delivered Dose Consistency

| | Liquid - Solid 100% LA + 50% Polymer | Liquid-Liquid 34.2% LA + 55.0% Polymer | |
|---|---|---|---|
| Mixing Cycles | 60 | 20 | 60 |
| N | 6 | 10 | 10 |
| Ave (% target) | 113.0 | 96.3 | 101.2 |
| Stdev (% target) | 1.5 | 3.4 | 2.5 |
| RSD (%) | 1.3 | 3.5 | 2.5 |

Figure 10:
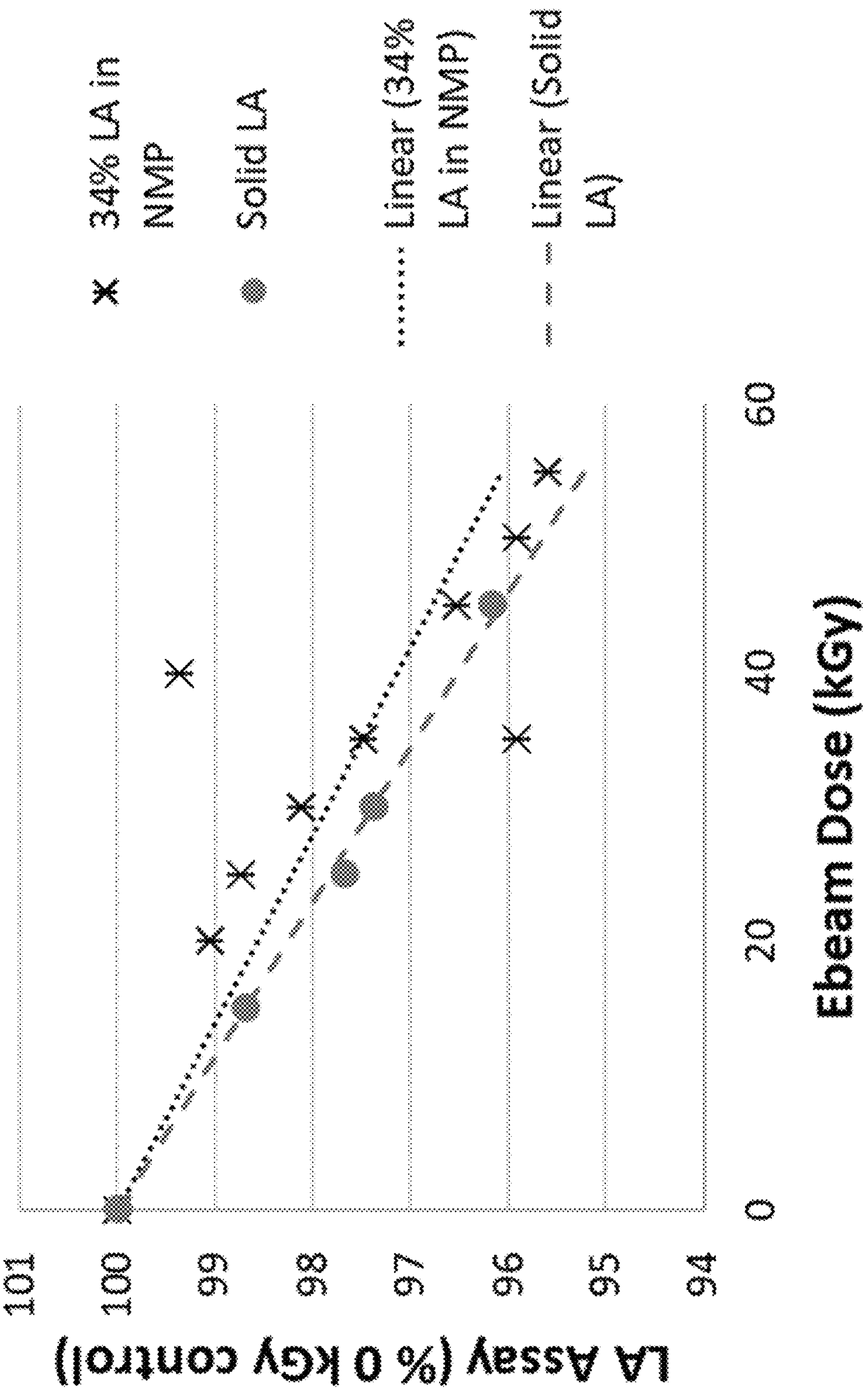
FIG. 10 is a plot of LA content versus e-beam dose for 34% LA in NMP as compared to solid LA.

To demonstrate improved stability of liquid-liquid formulations, the following experiments were conducted. Liquid drug syringes were prepared by dissolving LA in NMP, and then filled into syringes and packaging in foil pouches. Solid drug syringes were prepared by dissolving LA in water and gently mixing until dissolved. The LA solution was filled into male syringes, lyophilized to remove water, and then packaged in trays. Samples were irradiated by e-beam irradiation at the indicated target dose. The irradiated syringe was delivered and tested for LA content directly (not mixed with a polymer syringe). LA content was then expressed as a % of the non-irradiated control. A linear fit was applied to each data set with the intercept set to 100% (FIG. 10). While there was variability in results for the LA solution, the stability of leuprolide acetate to e-beam irradiation was generally similar or slightly better when in the drug solution than as a solid. This is surprising, as typically chemicals in solution are more reactive (and thus sensitive to degradation) than when in solid form.

Various modifications of the above-described disclosure will be evident to those skilled in the art. It is intended that such modifications are included within the scope of the following claims.

What is claimed is:

1. A pharmaceutical product comprising:

a first syringe filled with a polymer solution of from 50% to 60% by weight of a poly(D,L-lactide-co-glycolide) (PLG) dissolved in N-methyl-2-pyrrolidone (NMP), wherein PLG has a molar ratio of lactide to glycolide monomers of 85:15, and wherein PLG has a weight average molecular weight of from 15 kDa to 35 kDa; and a second syringe filled with a drug solution of from 40 mg to 50 mg of leuprolide acetate dissolved in NMP at a concentration of from 20% to 45% (w/w) of leuprolide acetate, wherein the drug solution remains a solution over the entire shelf life of the pharmaceutical product, wherein the shelf life is at least 24 months of storage at from 2° C. to 8° C.;

wherein the polymer and drug solutions of the first and second syringes are not mixed prior to use; and wherein when the polymer solution and the drug solution are mixed, the resulting composition is a homogenous extended-release composition for subcutaneous injection into a subject that upon injection into the subject, forms an in situ depot that releases leuprolide acetate over a time period of 6 months.

2. The pharmaceutical product of claim 1, wherein the drug solution concentration remains at from 20% to 45% (w/w) of leuprolide acetate during at least 6 months of storage at 25° C.

3. The pharmaceutical product of claim 1, wherein leuprolide acetate is dissolved in NMP in the drug solution at a concentration of from 30% to 44% (w/w) of leuprolide acetate.

4. The pharmaceutical product of claim 1, wherein leuprolide acetate is dissolved in NMP in the drug solution at a concentration of from 31% to 42% (w/w) of leuprolide acetate.

5. The pharmaceutical product of claim 1, wherein leuprolide acetate is dissolved in NMP in the drug solution at a concentration of from 20% to 44% (w/w) of leuprolide acetate.

6. The pharmaceutical product of claim 1, wherein leuprolide acetate is dissolved in NMP in the drug solution at a concentration of from 20% to 42% (w/w) of leuprolide acetate.

7. The pharmaceutical product of claim 1, wherein leuprolide acetate is dissolved in NMP in the drug solution at a concentration of from 20% to 41% (w/w) of leuprolide acetate.

8. The pharmaceutical product of claim 1, wherein leuprolide acetate is dissolved in NMP in the drug solution at a concentration of 30%, 31%, 32%, 33%, 34%, 35%, 36%, 37%, 38%, 39%, 40%, 41%, 42%, 43%, or 44% (w/w) of leuprolide acetate.

9. The pharmaceutical product of claim 1, wherein the polymer solution has a viscosity of from 3,000 cP to 20,000 cP at 25° C.

10. The pharmaceutical product of claim 1, wherein the polymer solution has a viscosity of from 10,000 cP to 20,000 cP at 25° C.

11. The pharmaceutical product of claim 1, wherein the first syringe is formulated to deliver from 100 mg to 170 mg of NMP and from 145 mg to 185 mg of PLG, and the second syringe is formulated to deliver 45 mg of leuprolide acetate and from 55 mg to 87.2 mg of NMP.

12. The pharmaceutical product of claim 11, wherein the first syringe is formulated to deliver from 160 mg to 170 mg of PLG.

13. The pharmaceutical product of claim 1, wherein the total amount of PLG in the homogeneous extended-release composition is from 20% to 45% by weight.

14. The pharmaceutical product of claim 1, wherein the total amount of NMP in the homogeneous extended-release composition is from 45% to 65% by weight.

15. The pharmaceutical product of claim 1, wherein PLG is 1,6-hexane-diol-initiated.

16. The pharmaceutical product of claim 1, wherein the pharmaceutical product is formulated to provide an extended release composition upon mixing the polymer and drug solutions of the first and second syringes which delivers 165 mg of PLG, 220 mg of NMP, and 45 mg of leuprolide acetate when administered to a subject by subcutaneous injection at a total injection volume of 0.43 mL.

17. A method of reducing luteinizing hormone levels in a subject with prostate cancer or central precocious puberty, the method comprising subcutaneously administering an extended release composition prepared by mixing the polymer and drug solutions of the first and second syringes of claim 1.

18. The method of claim 17, wherein the extended release composition is prepared by mixing the polymer and drug solutions of the first and second syringes using no more than 30 mixing cycles.

19. The method of claim 17, wherein the extended release composition is prepared by mixing the polymer and drug solutions of the first and second syringes using no more than 20 mixing cycles.

20. The method of claim 17, wherein the prostate cancer is advanced prostate cancer.

21. The method of claim 17, wherein administering the extended release composition: (a) reduces serum testosterone levels in a male subject with prostate cancer or central precocious puberty, or (b) reduces estrogen or estradiol levels, or follicle stimulating hormone levels, in a female subject with central precocious puberty.

22. The method of claim 17, wherein the extended release composition is administered once per every six months.

23. A kit comprising the pharmaceutical product of claim 1 together with instructions for mixing and administration.

24. The kit of claim 23, wherein the instructions describe (a) mixing the polymer solution of the first syringe with the drug solution of the second syringe for 30 cycles to form an extended release composition, and (b) administering the extended release composition to a subject by subcutaneous injection.

* * * * *